US007622251B2

(12) United States Patent
Baker et al.

(10) Patent No.: US 7,622,251 B2
(45) Date of Patent: Nov. 24, 2009

(54) MOLECULAR INDICATORS OF BREAST CANCER PROGNOSIS AND PREDICTION OF TREATMENT RESPONSE

(75) Inventors: Joffre B. Baker, Montara, CA (US); John L. Bryant, Allison Park, PA (US); Soonmyung Paik, Pittsburgh, PA (US); Steven Shak, Hillsborough, CA (US)

(73) Assignees: Genomic Health, Inc., Redwood City, CA (US); NSABP Foundation, Inc., Pittsburgh, PA (US)

( * ) Notice: Subject to any disclaimer, the term of this patent is extended or adjusted under 35 U.S.C. 154(b) by 0 days.

(21) Appl. No.: 11/267,807

(22) Filed: Nov. 4, 2005

(65) Prior Publication Data

US 2006/0166231 A1   Jul. 27, 2006

Related U.S. Application Data

(60) Provisional application No. 60/625,442, filed on Nov. 5, 2004.

(51) Int. Cl.
C12Q 1/68 (2006.01)
(52) U.S. Cl. ....................................................... 435/6
(58) Field of Classification Search ................... 435/6
See application file for complete search history.

(56) References Cited

U.S. PATENT DOCUMENTS

| | | | |
|---|---|---|---|
| 4,699,877 A | 10/1987 | Cline et al. .................. 435/6 |
| 4,968,603 A | 11/1990 | Slamon et al. ................ 435/6 |
| 5,015,568 A | 5/1991 | Tsujimoto et al. ............. 435/5 |
| 5,202,429 A | 4/1993 | Tsujimoto et al. ......... 536/23.5 |
| 5,459,251 A | 10/1995 | Tsujimoto et al. ......... 536/23.5 |
| RE35,491 E | 4/1997 | Cline et al. .................. 435/6 |
| 5,670,325 A | 9/1997 | Lapidus et al. ............... 435/6 |
| 5,741,650 A | 4/1998 | Lapidus et al. ............... 435/6 |
| 5,830,665 A | 11/1998 | Shuber et al. ................ 435/6 |
| 5,830,753 A | 11/1998 | Coulie et al. ............... 435/325 |
| 5,858,678 A | 1/1999 | Chinnadurai ................ 435/7.1 |
| 5,861,278 A | 1/1999 | Wong et al. ................ 435/69.1 |
| 5,928,870 A | 7/1999 | Lapidus et al. ............... 435/6 |
| 5,952,178 A | 9/1999 | Lapidus et al. ............... 435/6 |
| 5,952,179 A | 9/1999 | Chinnadurai ................. 435/6 |
| 5,962,312 A | 10/1999 | Plowman et al. .......... 435/320.1 |
| 5,985,553 A | 11/1999 | King et al. .................. 435/6 |
| 6,020,137 A | 2/2000 | Lapidus et al. ............... 435/6 |
| 6,100,029 A | 8/2000 | Lapidus et al. ............... 435/6 |
| 6,143,529 A | 11/2000 | Lapidus et al. ............. 435/91.2 |
| 6,146,828 A | 11/2000 | Lapidus et al. ............... 435/6 |
| 6,171,798 B1 | 1/2001 | Levine et al. ................ 435/6 |
| 6,203,993 B1 | 3/2001 | Shuber et al. ................ 435/6 |
| 6,207,401 B1 | 3/2001 | Plowman et al. ............. 435/15 |
| 6,207,452 B1 | 3/2001 | Govindaswamy ........... 435/330 |
| 6,214,558 B1 | 4/2001 | Shuber et al. ................ 435/6 |
| 6,245,523 B1 | 6/2001 | Altieri ..................... 435/69.1 |
| 6,248,535 B1 | 6/2001 | Danenberg et al. ............ 435/6 |
| 6,271,002 B1 | 8/2001 | Linsley et al. ............. 435/91.1 |
| 6,322,986 B1 | 11/2001 | Ross .......................... 435/6 |
| 6,414,134 B1 | 7/2002 | Reed ....................... 536/24.5 |
| 6,582,919 B2 | 6/2003 | Danenberg ................... 435/6 |
| 6,602,670 B2 | 8/2003 | Danenberg ................... 435/6 |
| 6,618,679 B2 | 9/2003 | Loehrlein et al. ............ 702/20 |
| 6,620,606 B2 | 9/2003 | Bandman et al. ............ 435/219 |
| 6,696,558 B2 | 2/2004 | Reed et al. ............... 536/23.5 |
| 6,716,575 B2 | 4/2004 | Plowman et al. ............. 435/6 |
| 6,750,013 B2 | 6/2004 | Gish et al. ................... 435/6 |
| 6,800,737 B2 | 10/2004 | Altieri ..................... 530/386 |
| 6,943,150 B1 | 9/2005 | Altieri ...................... 514/21 |
| 2002/0004491 A1 | 1/2002 | Xu et al. ..................... 514/44 |
| 2002/0009736 A1 | 1/2002 | Wang .......................... 435/6 |
| 2002/0039764 A1 | 4/2002 | Rosen ...................... 435/69.1 |
| 2002/0160395 A1 | 10/2002 | Altieri et al. ................. 435/6 |
| 2003/0073112 A1 | 4/2003 | Zhang et al. ................. 435/6 |

(Continued)

FOREIGN PATENT DOCUMENTS

| | | |
|---|---|---|
| EP | 0 108 564 B1 | 5/1988 |
| EP | 1 365 034 | 11/2003 |
| WO | WO 99/02714 | 1/1999 |
| WO | WO 00/50595 | 8/2000 |
| WO | WO 00/55173 | 9/2000 |

(Continued)

OTHER PUBLICATIONS

Kuukasjarvi et al (Journal of Clinical Oncology, "Loss of Estrogen Receptor in Recurrent Breast Cancer Is Associated With Poor Response to Endocrine Therapy", Sep. 1996, 14(9):2584-2589).*
Tockman et al (Cancer Res., 1992, 52:2711s-2718s).*
Gasparini et al (Clinical Cancer Research, Feb. 1995, 1: 189-198).*
Zhang et al (Clinical Cancer Research, Oct. 1999, 5: 2971-2977).*
Barrett-Lee et al (Cancer Research, Dec. 1987, 47:6653-6659).*
Vollenweider-Zerargui et al (Cancer, 1986, 57:1171-1180).*

(Continued)

*Primary Examiner*—Sean E Aeder
(74) *Attorney, Agent, or Firm*—James S. Keddie; Carol L. Francis; Bozicevic, Field & Francis LLP

(57) ABSTRACT

The present invention relates to quantitative molecular indicators that can guide clinical decisions in breast cancer, such as estrogen receptor (ESR1)-positive, lymph node-negative breast cancer. In particular, the invention concerns certain genes, the varied expression of which indicates the likelihood of recurrence of surgically resected breast cancer in patients who are not treated with a therapeutic agent in the adjuvant setting. In addition, the invention concerns the use of quantitative measurement of the expression of certain genes, including the ESR1 gene, that measure as a continuous variable, to determine (a) the likelihood of a beneficial response to the anti-estrogen therapeutic agent, such as tamoxifen; and (b) the potential magnitude of beneficial response to chemotherapy.

12 Claims, 2 Drawing Sheets

U.S. PATENT DOCUMENTS

| | | |
|---|---|---|
| 2003/0104499 A1 | 6/2003 | Pressman et al. ............ 435/7.23 |
| 2003/0165952 A1 | 9/2003 | Linnarsson et al. ............. 435/6 |
| 2003/0180791 A1 | 9/2003 | Chinnadurai ................... 435/6 |
| 2003/0198970 A1 | 10/2003 | Roberts ......................... 435/6 |
| 2003/0198972 A1 | 10/2003 | Erlander et al. ................ 435/6 |
| 2003/0219771 A1 | 11/2003 | Bevilacqua et al. ............. 435/6 |
| 2003/0229455 A1 | 12/2003 | Bevilacqua et al. ........... 702/20 |
| 2004/0009489 A1 | 1/2004 | Golub et al. .................... 435/6 |
| 2004/0126775 A1 | 7/2004 | Altieri et al. ................... 435/6 |
| 2004/0133352 A1 | 7/2004 | Bevilacqua et al. ........... 702/19 |
| 2005/0048542 A1 | 3/2005 | Baker et al. .................... 435/6 |

FOREIGN PATENT DOCUMENTS

| | | |
|---|---|---|
| WO | WO 01/25250 | 4/2001 |
| WO | WO 01/40466 | 6/2001 |
| WO | WO 01/55320 | 8/2001 |
| WO | WO 01/70979 | 9/2001 |
| WO | WO 02/00677 | 1/2002 |
| WO | WO 02/06526 | 1/2002 |
| WO | WO 02/08260 | 1/2002 |
| WO | WO 02/08261 | 1/2002 |
| WO | WO 02/08282 | 1/2002 |
| WO | WO 02/08765 | 1/2002 |
| WO | WO 02/46467 | 6/2002 |
| WO | WO 02/017852 | 7/2002 |
| WO | WO 02/055988 | 7/2002 |
| WO | WO 02/059377 | 8/2002 |
| WO | WO 02/068579 | 9/2002 |
| WO | WO 02/103320 | 12/2002 |
| WO | WO 03/011897 | 2/2003 |
| WO | WO 03/078662 | 9/2003 |
| WO | WO 03/083096 | 10/2003 |
| WO | WO 2004/065583 | 8/2004 |

OTHER PUBLICATIONS

Carmeci et al (Am J Pathol, May 1997, 150(5): 1563-70).*

Brabender, Jan, et al.; *Epidermal Growth Factor Receptor and HER2-neu mRNA Expression in Non-Small Cell Lung Cancer Is Correlated with Survival*, Clinical Cancer Research; vol. 7, Jul. 2001; pp. 1850-1855.

Ding, Chunming, et al.; *A high-throughput gene expression analysis technique using competitive PCR and matrix-assisted laser desorption ionization time-of-flight MS*, PNAS, vol. 100:6; Mar. 18, 2003; pp. 3059-3064.

Cambridge Healthtech Institute Conference Agenda; "Enabling Molecular Profiling With Cellular Resolution: Microgenomics Using Homogeneous Cell Samples"; Dec. 2002; 5 pgs.

Yang, Li, et al.; *BADGE, BeadsArray for the Detection of Gene Expression, a High-Throughput Diagnostic Bioassay*; Genome Research; vol. 11; 2001; pp. 1888-1898.

Ayers, M. et al., "Gene Expression Profiles Predict Complete Pathologic Response to Neoadjuvant Paclitaxel and Fluorouracil, Doxorubicin, and Cyclophosphamide Chemotherapy in Breast Cancer," *Journal of Clinical Oncology*, 22:(12), 2004, pp. 2284-2293.

Garber, K. et al., "Gene Expression Tests Foretell Breast Cancer's Future," *Science*, 303:(5665), 2004, pp. 1754-1755.

Jansen, M. et al., Molecular Classification of Tamoxifen-Responsive and -Resistant Breast Carcinomas by Gene Expression Profiling, *Breast Cancer Research and Treatment*, 82:(Supplement 1.), 2003, p. S14.

Los, G. et al., "Using mRNA Expression Profiling to Determine Anticancer Drug Efficacy," *Cytometry*, 47:(1), 2002, pp. 66-71.

Paik, S. et al., "A Multigene Assay to Predict Recurrence of Tamoxifen-Treated, Node-Negative Breast Cancer," *The New England Journal of Medicine*, 351:(27), 2004, pp. 2817-2826.

Paik, S. et al., "Multi-Gene RT-PCR Assay for Predicting Recurrence in Node Negative Breast Cancer Patients-NSABP Studies B-20 and B-14," *Breast Cancer Research and Treatment*, 82:(Supplement 1.), 2003, pp. S10-S11.

Ravdin, P.M. et al., "Computer Program to Assist in Making Decisions about Adjuvant Therapy for Women with Early Breast Cancer," *Journal of Clinical Oncology*, 19:(4), 2001, pp. 980-991.

Fisher, B., et al. Relative worth of estrogen or progesterone receptor and pathologic characteristics of differentiation as indicators of prognosis in node negative breast cancer patients: Findings from national surgical adjuvant breast and bowel project protocol B-06. Journal of Clinical Oncology. 1988, vol. 6, No. 7, pp. 1076-1087.

Kononen, J., et al. Tissue microarrays for high-throughput molecular profiling of tumor specimens. Nature Medicine. 1998, vol. 4, No. 7, pp. 844-847.

Lah, T., et al. Cathepsin B, a prognostic indicator in lymph node-negative breast carcinoma patients: Comparison with cathepsin D, cathepsin L, and other clinical indicators. Clinical Cancer Research. 2000, vol. 6, pp. 578-584.

Miyoshi, Y., et al. Association of centrosomal kinase STK15/BTAK MRNA expression with chromosomal instability in human breast cancers. 2001, vol. 92, pp. 370-373.

Modlich, O., et al. Predictors of primary breast cancers responsiveness to preoperative epirubicin/cyclophosphamide-based chemotherapy: translation of microarray data into clinically useful predictive signatures. Journal of Translational Medicine. 2005, vol. 3 pp. 32.

Nakopoulou, L., et al. Stromelysin-3 protein expression in invasive breast cancer: Relation to proliferation, cell survival and patients' outcome. Modern Pathology. 2002, vol. 15, No. 11, pp. 1154-1161.

Nishidate, T., et al. Genome-wide gene-expression profiles of breast-cancer cells purified with laser microbeam microdissection: Identification of genes associated with progression and metastasis. International Journal of Oncology. 2004, vol. 25, pp. 797-819.

Reiner, A., et al. Immunocytochemical localization of estrogen and progesterone receptor and prognosis in human primary breast cancer. Cancer Research. 1990, vol. 50, pp. 7057-7061.

Rundle, A., et al. The association between glutathione S-transferase M1 genotype and polycyclic aromatic hydrocarbon-DNA adducts in breast tissue. Cancer, Epidemiology, Biomarkers, and Prevention. 2000, vol. 9, pp. 1079-1085.

Shen, R., et al. Prognostic meta-signature of breast cancer developed by two-stage mixture modeling of microarray data. BMC Genomics. 2004, vol. 5, pp. 94.

Slamon, D., et al. Human breast cancer: Correlation of relapse and survival with amplification of the HER-2/neu oncogene. Science. 1987, vol. 235, No. 4785, pp. 177-182.

Sorlie, T., et al. Gene expression patterns of breast carcinomas distinguish tumor subclasses with clinical implications. PNAS. 2001, vol. 98, No. 19, pp. 10869-10874.

Stefano, R., et al. Expression levels and clinical-pathological correlations of HER2/neu in primary and metastatic human breast cancer. Annuals of the New York Academy of Sciences. 2004, vol. 1028, pp. 463-172.

Tanaka, K., et al. Expression of survivin and its relationship to loss of apoptosis in breast carcinomas. Clinical Cancer Research. 2000, vol. 6, pp. 127-134.

Turner, B., et al. BAG-1: A novel biomarker predicting long-term survival in early-stage breast cancer. Journal of Clinical Oncology. 2001, vol. 19, No. 4, pp. 992-1000.

Urruticoechea, A., et al. Proliferation marker in Ki-67 in early breast cancer. Journal of Clinical Oncology. 2005, vol. 23, No. 28, pp. 7212-7220.

Van't Veer, L., et al. Gene expression profiling predicts clinical outcome of breast cancer. Nature. 2002, vol. 415, pp. 530-536.

* cited by examiner

SEQUENCE LISTING

<160> NUMBER OF SEQ ID NOS: 84

<210> SEQ ID NO 1
<211> LENGTH: 21
<212> TYPE: DNA
<213> ORGANISM: Artificial Sequence
<220> FEATURE:
<223> OTHER INFORMATION: Synthetic Oligonucleotide Forward Primer

<400> SEQUENCE: 1
cagcagatgt ggatcagcaa g                                              21

<210> SEQ ID NO 2
<211> LENGTH: 18
<212> TYPE: DNA
<213> ORGANISM: Artificial Sequence
<220> FEATURE:

```
<223> OTHER INFORMATION: Synthetic Oligonucleotide Reverse Primer

<400> SEQUENCE: 2
gcatttgcgg tggacgat                                                 18

<210> SEQ ID NO 3
<211> LENGTH: 23
<212> TYPE: DNA
<213> ORGANISM: Artificial Sequence
<220> FEATURE:
<223> OTHER INFORMATION: Synthetic Oligonucleotide Probe

<400> SEQUENCE: 3
aggagtatga cgagtccggc ccc                                           23

<210> SEQ ID NO 4
<211> LENGTH: 23
<212> TYPE: DNA
<213> ORGANISM: Artificial Sequence
<220> FEATURE:
<223> OTHER INFORMATION: Synthetic Oligonucleotide Forward Primer

<400> SEQUENCE: 4
cgttgtcagc acttggaata caa                                           23

<210> SEQ ID NO 5
<211> LENGTH: 24
<212> TYPE: DNA
<213> ORGANISM: Artificial Sequence
<220> FEATURE:
<223> OTHER INFORMATION: Synthetic Oligonucleotide Reverse Primer

<400> SEQUENCE: 5
gttcaacctc ttcctgtgga ctgt                                          24

<210> SEQ ID NO 6
<211> LENGTH: 26
<212> TYPE: DNA
<213> ORGANISM: Artificial Sequence
<220> FEATURE:
<223> OTHER INFORMATION: Synthetic Oligonucleotide Probe

<400> SEQUENCE: 6
cccaattaac atgacccggc aaccat                                        26

<210> SEQ ID NO 7
<211> LENGTH: 25
<212> TYPE: DNA
<213> ORGANISM: Artificial Sequence
<220> FEATURE:
<223> OTHER INFORMATION: Synthetic Oligonucleotide Forward Primer

<400> SEQUENCE: 7
cagatggacc tagtacccac tgaga                                         25

<210> SEQ ID NO 8
<211> LENGTH: 24
<212> TYPE: DNA
<213> ORGANISM: Artificial Sequence
<220> FEATURE:
<223> OTHER INFORMATION: Synthetic Oligonucleotide Reverse Primer

<400> SEQUENCE: 8
cctatgattt aagggcattt ttcc                                          24
```

```
<210> SEQ ID NO 9
<211> LENGTH: 22
<212> TYPE: DNA
<213> ORGANISM: Artificial Sequence
<220> FEATURE:
<223> OTHER INFORMATION: Synthetic Oligonucleotide Probe

<400> SEQUENCE: 9
ttccacgccg aaggacagcg at                                              22

<210> SEQ ID NO 10
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 10
ttcaggttgt tgcaggagac                                                 20

<210> SEQ ID NO 11
<211> LENGTH: 20
<212> TYPE: DNA
<213> ORGANISM: Artificial Sequence
<220> FEATURE:
<223> OTHER INFORMATION: Synthetic Oligonucleotide Reverse Primer

<400> SEQUENCE: 11
catcttcttg ggcacacaat                                                 20

<210> SEQ ID NO 12
<211> LENGTH: 27
<212> TYPE: DNA
<213> ORGANISM: Artificial Sequence
<220> FEATURE:
<223> OTHER INFORMATION: Synthetic Oligonucleotide Probe

<400> SEQUENCE: 12
tgtctccatt attgatcggt tcatgca                                         27

<210> SEQ ID NO 13
<211> LENGTH: 18
<212> TYPE: DNA
<213> ORGANISM: Artificial Sequence
<220> FEATURE:
<223> OTHER INFORMATION: Synthetic Oligonucleotide Forward Primer

<400> SEQUENCE: 13
tggttcccag ccctgtgt                                                   18

<210> SEQ ID NO 14
<211> LENGTH: 19
<212> TYPE: DNA
<213> ORGANISM: Artificial Sequence
<220> FEATURE:
<223> OTHER INFORMATION: Synthetic Oligonucleotide Reverse Primer

<400> SEQUENCE: 14
ctcctccacc ctgggttgt                                                  19

<210> SEQ ID NO 15
<211> LENGTH: 28
<212> TYPE: DNA
<213> ORGANISM: Artificial Sequence
<220> FEATURE:
<223> OTHER INFORMATION: Synthetic Oligonucleotide Probe
```

```
<400> SEQUENCE: 15
ctccaagccc agattcagat tcgagtca                                          28

<210> SEQ ID NO 16
<211> LENGTH: 21
<212> TYPE: DNA
<213> ORGANISM: Artificial Sequence
<220> FEATURE:
<223> OTHER INFORMATION: Synthetic Oligonucleotide Forward Primer

<400> SEQUENCE: 16
tgacaatcag cacacctgca t                                                 21

<210> SEQ ID NO 17
<211> LENGTH: 23
<212> TYPE: DNA
<213> ORGANISM: Artificial Sequence
<220> FEATURE:
<223> OTHER INFORMATION: Synthetic Oligonucleotide Reverse Primer

<400> SEQUENCE: 17
tgtgactaca gccgtgatcc tta                                               23

<210> SEQ ID NO 18
<211> LENGTH: 20
<212> TYPE: DNA
<213> ORGANISM: Artificial Sequence
<220> FEATURE:
<223> OTHER INFORMATION: Synthetic Oligonucleotide Probe

<400> SEQUENCE: 18
caggccctct tccgagcggt                                                   20

<210> SEQ ID NO 19
<211> LENGTH: 21
<212> TYPE: DNA
<213> ORGANISM: Artificial Sequence
<220> FEATURE:
<223> OTHER INFORMATION: Synthetic Oligonucleotide Forward Primer

<400> SEQUENCE: 19
tgtctcactg agcgagcaga a                                                 21

<210> SEQ ID NO 20
<211> LENGTH: 19
<212> TYPE: DNA
<213> ORGANISM: Artificial Sequence
<220> FEATURE:
<223> OTHER INFORMATION: Synthetic Oligonucleotide Reverse Primer

<400> SEQUENCE: 20
accattgcag ccctgattg                                                    19

<210> SEQ ID NO 21
<211> LENGTH: 24
<212> TYPE: DNA
<213> ORGANISM: Artificial Sequence
<220> FEATURE:
<223> OTHER INFORMATION: Synthetic Oligonucleotide Probe

<400> SEQUENCE: 21
cttgaggacg cgaacagtcc acca                                              24

<210> SEQ ID NO 22
<211> LENGTH: 19
```

```
<212> TYPE: DNA
<213> ORGANISM: Artificial Sequence
<220> FEATURE:
<223> OTHER INFORMATION: Synthetic Oligonucleotide Forward Primer

<400> SEQUENCE: 22
cgtggtgccc ctctatgac                                                  19

<210> SEQ ID NO 23
<211> LENGTH: 19
<212> TYPE: DNA
<213> ORGANISM: Artificial Sequence
<220> FEATURE:
<223> OTHER INFORMATION: Synthetic Oligonucleotide Reverse Primer

<400> SEQUENCE: 23
ggctagtggg cgcatgtag                                                  19

<210> SEQ ID NO 24
<211> LENGTH: 19
<212> TYPE: DNA
<213> ORGANISM: Artificial Sequence
<220> FEATURE:
<223> OTHER INFORMATION: Synthetic Oligonucleotide Probe

<400> SEQUENCE: 24
ctggagatgc tggacgccc                                                  19

<210> SEQ ID NO 25
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 25
attccaccca tggcaaattc                                                 20

<210> SEQ ID NO 26
<211> LENGTH: 22
<212> TYPE: DNA
<213> ORGANISM: Artificial Sequence
<220> FEATURE:
<223> OTHER INFORMATION: Synthetic Oligonucleotide Reverse Primer

<400> SEQUENCE: 26
gatgggattt ccattgatga ca                                              22

<210> SEQ ID NO 27
<211> LENGTH: 22
<212> TYPE: DNA
<213> ORGANISM: Artificial Sequence
<220> FEATURE:
<223> OTHER INFORMATION: Synthetic Oligonucleotide Probe

<400> SEQUENCE: 27
ccgttctcag ccttgacggt gc                                              22

<210> SEQ ID NO 28
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 28
```
ccatctgcat ccatcttgtt                                                20

<210> SEQ ID NO 29
<211> LENGTH: 20
<212> TYPE: DNA
<213> ORGANISM: Artificial Sequence
<220> FEATURE:
<223> OTHER INFORMATION: Synthetic Oligonucleotide Reverse Primer

<400> SEQUENCE: 29
ggccaccagg gtattatctg                                                20

<210> SEQ ID NO 30
<211> LENGTH: 23
<212> TYPE: DNA
<213> ORGANISM: Artificial Sequence
<220> FEATURE:
<223> OTHER INFORMATION: Synthetic Oligonucleotide Probe

<400> SEQUENCE: 30
ctccccaccc ttgagaagtg cct                                            23

<210> SEQ ID NO 31
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 31
ggcccagctt gaattttca                                                 20

<210> SEQ ID NO 32
<211> LENGTH: 27
<212> TYPE: DNA
<213> ORGANISM: Artificial Sequence
<220> FEATURE:
<223> OTHER INFORMATION: Synthetic Oligonucleotide Reverse Primer

<400> SEQUENCE: 32
aagctatgag gaaagaagt acacgat                                         27

<210> SEQ ID NO 33
<211> LENGTH: 30
<212> TYPE: DNA
<213> ORGANISM: Artificial Sequence
<220> FEATURE:
<223> OTHER INFORMATION: Synthetic Oligonucleotide Probe

<400> SEQUENCE: 33
tcagccactg gcttctgtca taatcaggag                                     30

<210> SEQ ID NO 34
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 34
cccactcagt agccaagtca                                                20

<210> SEQ ID NO 35
<211> LENGTH: 20
<212> TYPE: DNA
<213> ORGANISM: Artificial Sequence

```
<220> FEATURE:
<223> OTHER INFORMATION: Synthetic Oligonucleotide Reverse Primer

<400> SEQUENCE: 35
cacgcaggtg gtatcagtct                                                    20

<210> SEQ ID NO 36
<211> LENGTH: 27
<212> TYPE: DNA
<213> ORGANISM: Artificial Sequence
<220> FEATURE:
<223> OTHER INFORMATION: Synthetic Oligonucleotide Probe

<400> SEQUENCE: 36
tcaagtaaac gggctgtttt ccaaaca                                            27

<210> SEQ ID NO 37
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 37
cggtgtgaga agtgcagcaa                                                    20

<210> SEQ ID NO 38
<211> LENGTH: 19
<212> TYPE: DNA
<213> ORGANISM: Artificial Sequence
<220> FEATURE:
<223> OTHER INFORMATION: Synthetic Oligonucleotide Reverse Primer

<400> SEQUENCE: 38
cctctcgcaa gtgctccat                                                     19

<210> SEQ ID NO 39
<211> LENGTH: 24
<212> TYPE: DNA
<213> ORGANISM: Artificial Sequence
<220> FEATURE:
<223> OTHER INFORMATION: Synthetic Oligonucleotide Probe

<400> SEQUENCE: 39
ccagaccata gcacactcgg gcac                                               24

<210> SEQ ID NO 40
<211> LENGTH: 19
<212> TYPE: DNA
<213> ORGANISM: Artificial Sequence
<220> FEATURE:
<223> OTHER INFORMATION: Synthetic Oligonucleotide Forward Primer

<400> SEQUENCE: 40
cggactttgg gtgcgactt                                                     19

<210> SEQ ID NO 41
<211> LENGTH: 24
<212> TYPE: DNA
<213> ORGANISM: Artificial Sequence
<220> FEATURE:
<223> OTHER INFORMATION: Synthetic Oligonucleotide Reverse Primer

<400> SEQUENCE: 41
ttacaactct tccactggga cgat                                               24
```

<210> SEQ ID NO 42
<211> LENGTH: 23
<212> TYPE: DNA
<213> ORGANISM: Artificial Sequence
<220> FEATURE:
<223> OTHER INFORMATION: Synthetic Oligonucleotide Probe

<400> SEQUENCE: 42
ccacttgtcg aaccaccgct cgt                                          23

<210> SEQ ID NO 43
<211> LENGTH: 18
<212> TYPE: DNA
<213> ORGANISM: Artificial Sequence
<220> FEATURE:
<223> OTHER INFORMATION: Synthetic Oligonucleotide Forward Primer

<400> SEQUENCE: 43
gccgagatcg ccaagatg                                                18

<210> SEQ ID NO 44
<211> LENGTH: 27
<212> TYPE: DNA
<213> ORGANISM: Artificial Sequence
<220> FEATURE:
<223> OTHER INFORMATION: Synthetic Oligonucleotide Reverse Primer

<400> SEQUENCE: 44
cttttgatgg tagagttcca gtgattc                                      27

<210> SEQ ID NO 45
<211> LENGTH: 24
<212> TYPE: DNA
<213> ORGANISM: Artificial Sequence
<220> FEATURE:
<223> OTHER INFORMATION: Synthetic Oligonucleotide Probe

<400> SEQUENCE: 45
cagcattgtc tgtcctccct ggca                                         24

<210> SEQ ID NO 46
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 46
gcatcaggct gtcattatgg                                              20

<210> SEQ ID NO 47
<211> LENGTH: 20
<212> TYPE: DNA
<213> ORGANISM: Artificial Sequence
<220> FEATURE:
<223> OTHER INFORMATION: Synthetic Oligonucleotide Reverse Primer

<400> SEQUENCE: 47
agtagttgtg ctgcccttcc                                              20

<210> SEQ ID NO 48
<211> LENGTH: 28
<212> TYPE: DNA
<213> ORGANISM: Artificial Sequence
<220> FEATURE:
<223> OTHER INFORMATION: Synthetic Oligonucleotide Probe

<400> SEQUENCE: 48
tgtccttacc tgtgggagct gtaaggtc					28

<210> SEQ ID NO 49
<211> LENGTH: 24
<212> TYPE: DNA
<213> ORGANISM: Artificial Sequence
<220> FEATURE:
<223> OTHER INFORMATION: Synthetic Oligonucleotide Forward Primer

<400> SEQUENCE: 49
ccattctatc atcaacgggt acaa					24

<210> SEQ ID NO 50
<211> LENGTH: 23
<212> TYPE: DNA
<213> ORGANISM: Artificial Sequence
<220> FEATURE:
<223> OTHER INFORMATION: Synthetic Oligonucleotide Reverse Primer

<400> SEQUENCE: 50
tcagcaagtg ggaaggtgta atc					23

<210> SEQ ID NO 51
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 51
tctccacaga caaggccagg actcg					25

<210> SEQ ID NO 52
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 52
catcttccag gaggaccact					20

<210> SEQ ID NO 53
<211> LENGTH: 20
<212> TYPE: DNA
<213> ORGANISM: Artificial Sequence
<220> FEATURE:
<223> OTHER INFORMATION: Synthetic Oligonucleotide Reverse Primer

<400> SEQUENCE: 53
tccgaccttc aatcatttca					20

<210> SEQ ID NO 54
<211> LENGTH: 24
<212> TYPE: DNA
<213> ORGANISM: Artificial Sequence
<220> FEATURE:
<223> OTHER INFORMATION: Synthetic Oligonucleotide Probe

<400> SEQUENCE: 54
ctctgtggca ccctggacta cctg					24

<210> SEQ ID NO 55

```
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 55
cctggaggct gcaacatacc                                              20

<210> SEQ ID NO 56
<211> LENGTH: 23
<212> TYPE: DNA
<213> ORGANISM: Artificial Sequence
<220> FEATURE:
<223> OTHER INFORMATION: Synthetic Oligonucleotide Reverse Primer

<400> SEQUENCE: 56
tacaatggct ttggaggata gca                                          23

<210> SEQ ID NO 57
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 57
atcctcctga agcccttttc gcagc                                        25

<210> SEQ ID NO 58
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 58
tgttttgatt cccgggctta                                              20

<210> SEQ ID NO 59
<211> LENGTH: 24
<212> TYPE: DNA
<213> ORGANISM: Artificial Sequence
<220> FEATURE:
<223> OTHER INFORMATION: Synthetic Oligonucleotide Reverse Primer

<400> SEQUENCE: 59
caaagctgtc agctctagca aaag                                         24

<210> SEQ ID NO 60
<211> LENGTH: 28
<212> TYPE: DNA
<213> ORGANISM: Artificial Sequence
<220> FEATURE:
<223> OTHER INFORMATION: Synthetic Oligonucleotide Probe

<400> SEQUENCE: 60
tgccttcttc ctccctcact tctcacct                                     28

<210> SEQ ID NO 61
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 61
```

```
gccaactgct ttcatttgtg                                              20

<210> SEQ ID NO 62
<211> LENGTH: 20
<212> TYPE: DNA
<213> ORGANISM: Artificial Sequence
<220> FEATURE:
<223> OTHER INFORMATION: Synthetic Oligonucleotide Reverse Primer

<400> SEQUENCE: 62
actcaggccc atttccttta                                              20

<210> SEQ ID NO 63
<211> LENGTH: 28
<212> TYPE: DNA
<213> ORGANISM: Artificial Sequence
<220> FEATURE:
<223> OTHER INFORMATION: Synthetic Oligonucleotide Probe

<400> SEQUENCE: 63
agggatctga accaatacag agcagaca                                     28

<210> SEQ ID NO 64
<211> LENGTH: 66
<212> TYPE: DNA
<213> ORGANISM: Artificial Sequence
<220> FEATURE:
<223> OTHER INFORMATION: Amplicon Sequence

<400> SEQUENCE: 64
cagcagatgt ggatcagcaa gcaggagtat gacgagtccg gcccctccat cgtccaccgc   60
aaatgc                                                             66

<210> SEQ ID NO 65
<211> LENGTH: 81
<212> TYPE: DNA
<213> ORGANISM: Artificial Sequence
<220> FEATURE:
<223> OTHER INFORMATION: Amplicon Sequence

<400> SEQUENCE: 65
cgttgtcagc acttggaata caagatggtt gccgggtcat gttaattggg aaaagaaca    60 gtccacagga agaggttgaa c                                            81

<210> SEQ ID NO 66
<211> LENGTH: 73
<212> TYPE: DNA
<213> ORGANISM: Artificial Sequence
<220> FEATURE:
<223> OTHER INFORMATION: Amplicon Sequence

<400> SEQUENCE: 66
cagatggacc tagtacccac tgagatttcc acgccgaagg acagcgatgg gaaaaatgcc   60
cttaaatcat agg                                                     73

<210> SEQ ID NO 67
<211> LENGTH: 84
<212> TYPE: DNA
<213> ORGANISM: Artificial Sequence
<220> FEATURE:
<223> OTHER INFORMATION: Amplicon Sequence

<400> SEQUENCE: 67
```

```
ttcaggttgt tgcaggagac catgtacatg actgtctcca ttattgatcg gttcatgcag      60
aataattgtg tgcccaagaa gatg                                             84
```

<210> SEQ ID NO 68
<211> LENGTH: 74
<212> TYPE: DNA
<213> ORGANISM: Artificial Sequence
<220> FEATURE:
<223> OTHER INFORMATION: Amplicon Sequence

<400> SEQUENCE: 68

```
tggttcccag ccctgtgtcc acctccaagc ccagattcag attcgagtca tgtacacaac      60
ccagggtgga ggag                                                        74
```

<210> SEQ ID NO 69
<211> LENGTH: 77
<212> TYPE: DNA
<213> ORGANISM: Artificial Sequence
<220> FEATURE:
<223> OTHER INFORMATION: Amplicon Sequence

<400> SEQUENCE: 69

```
tgacaatcag cacacctgca ttcaccgctc ggaagagggc ctgagctgca tgaataagga      60
tcacggctgt agtcaca                                                     77
```

<210> SEQ ID NO 70
<211> LENGTH: 67
<212> TYPE: DNA
<213> ORGANISM: Artificial Sequence
<220> FEATURE:
<223> OTHER INFORMATION: Amplicon Sequence

<400> SEQUENCE: 70

```
tgtctcactg agcgagcaga atctggtgga ctgttcgcgt cctcaaggca atcagggctg      60
caatggt                                                                67
```

<210> SEQ ID NO 71
<211> LENGTH: 68
<212> TYPE: DNA
<213> ORGANISM: Artificial Sequence
<220> FEATURE:
<223> OTHER INFORMATION: Amplicon Sequence

<400> SEQUENCE: 71

```
cgtggtgccc ctctatgacc tgctgctgga gatgctggac gcccaccgcc tacatgcgcc      60
cactagcc                                                               68
```

<210> SEQ ID NO 72
<211> LENGTH: 74
<212> TYPE: DNA
<213> ORGANISM: Artificial Sequence
<220> FEATURE:
<223> OTHER INFORMATION: Amplicon Sequence

<400> SEQUENCE: 72

```
attccaccca tggcaaattc catggcaccg tcaaggctga gaacgggaag cttgtcatca      60
atggaaatcc catc                                                        74
```

<210> SEQ ID NO 73
<211> LENGTH: 67
<212> TYPE: DNA
<213> ORGANISM: Artificial Sequence

```
<220> FEATURE:
<223> OTHER INFORMATION: Amplicon Sequence

<400> SEQUENCE: 73
ccatctgcat ccatcttgtt tgggctcccc acccttgaga agtgcctcag ataatacect    60 ggtggcc                                                              67

<210> SEQ ID NO 74
<211> LENGTH: 86
<212> TYPE: DNA
<213> ORGANISM: Artificial Sequence
<220> FEATURE:
<223> OTHER INFORMATION: Amplicon Sequence

<400> SEQUENCE: 74
aagctatgag gaaaagaagt acacgatggg ggacgctcct gattatgaca gaagccagtg    60
gctgaatgaa aaattcaagc tgggcc                                         86

<210> SEQ ID NO 75
<211> LENGTH: 73
<212> TYPE: DNA
<213> ORGANISM: Artificial Sequence
<220> FEATURE:
<223> OTHER INFORMATION: Amplicon Sequence

<400> SEQUENCE: 75
cccactcagt agccaagtca caatgtttgg aaaacagccc gtttacttga gcaagactga    60
taccacctgc gtg                                                       73

<210> SEQ ID NO 76
<211> LENGTH: 70
<212> TYPE: DNA
<213> ORGANISM: Artificial Sequence
<220> FEATURE:
<223> OTHER INFORMATION: Amplicon Sequence

<400> SEQUENCE: 76
cggtgtgaga agtgcagcaa gccctgtgcc cgagtgtgct atggtctggg catggagcac    60
ttgcgagagg                                                           70

<210> SEQ ID NO 77
<211> LENGTH: 80
<212> TYPE: DNA
<213> ORGANISM: Artificial Sequence
<220> FEATURE:
<223> OTHER INFORMATION: Amplicon Sequence

<400> SEQUENCE: 77
cggactttgg gtgcgacttg acgagcggtg gttcgacaag tggccttgcg ggccggatcg    60
tcccagtgga agagttgtaa                                                80

<210> SEQ ID NO 78
<211> LENGTH: 74
<212> TYPE: DNA
<213> ORGANISM: Artificial Sequence
<220> FEATURE:
<223> OTHER INFORMATION: Amplicon Sequence

<400> SEQUENCE: 78
gccgagatcg ccaagatgtt gccagggagg acagacaatg ctgtgaagaa tcactggaac    60
tctaccatca aaag                                                      74
```

<210> SEQ ID NO 79
<211> LENGTH: 85
<212> TYPE: DNA
<213> ORGANISM: Artificial Sequence
<220> FEATURE:
<223> OTHER INFORMATION: Amplicon Sequence

<400> SEQUENCE: 79
gcatcaggct gtcattatgg tgtccttacc tgtgggagct gtaaggtctt ctttaagagg    60
gcaatggaag ggcagcacaa ctact                                         85

<210> SEQ ID NO 80
<211> LENGTH: 75
<212> TYPE: DNA
<213> ORGANISM: Artificial Sequence
<220> FEATURE:
<223> OTHER INFORMATION: Amplicon Sequence

<400> SEQUENCE: 80
ccattctatc atcaacgggt acaaacgagt cctggccttg tctgtggaga cggattacac    60
cttcccactt gctga                                                    75

<210> SEQ ID NO 81
<211> LENGTH: 69
<212> TYPE: DNA
<213> ORGANISM: Artificial Sequence
<220> FEATURE:
<223> OTHER INFORMATION: Amplicon Sequence

<400> SEQUENCE: 81
catcttccag gaggaccact ctctgtggca ccctggacta cctgccccct gaaatgattg    60
aaggtcgga                                                           69

<210> SEQ ID NO 82
<211> LENGTH: 90
<212> TYPE: DNA
<213> ORGANISM: Artificial Sequence
<220> FEATURE:
<223> OTHER INFORMATION: Amplicon Sequence

<400> SEQUENCE: 82
cctggaggct gcaacatacc tcaatcctgt cccaggccgg atcctcctga agcccttttc    60
gcagcactgc tatcctccaa agccattgta                                    90

<210> SEQ ID NO 83
<211> LENGTH: 80
<212> TYPE: DNA
<213> ORGANISM: Artificial Sequence
<220> FEATURE:
<223> OTHER INFORMATION: Amplicon Sequence

<400> SEQUENCE: 83
tgttttgatt cccgggctta ccaggtgaga agtgagggag gaagaaggca gtgtcccttt    60
tgctagagct gacagctttg                                               80

<210> SEQ ID NO 84
<211> LENGTH: 68
<212> TYPE: DNA
<213> ORGANISM: Artificial Sequence
<220> FEATURE:
<223> OTHER INFORMATION: Amplicon Sequence

<400> SEQUENCE: 84

```
gccaactgct ttcatttgtg agggatctga accaatacag agcagacata aaggaaatgg    60
gcctgagt                                                              68
```

MOLECULAR INDICATORS OF BREAST CANCER PROGNOSIS AND PREDICTION OF TREATMENT RESPONSE

This application claims priority under 35 U.S.C. §119(e) to provisional application Ser. No. 60/625,442 filed on Nov. 5, 2004, the entire disclosure of which is hereby expressly incorporated by reference.

FIELD OF THE INVENTION

The present invention relates to quantitative molecular indicators that can guide clinical decisions in breast cancer, such as estrogen receptor (ESR1)-positive, lymph node-negative breast cancer. In particular, the invention concerns certain genes, the varied expression of which indicates the likelihood of recurrence of surgically resected breast cancer in patients who are not treated with a therapeutic agent in the adjuvant setting. In addition, the invention concerns the use of quantitative measurement of the expression of certain genes, including the ESR1 gene, that measure as a continuous variable, to determine (a) the likelihood of a beneficial response to the anti-estrogen therapeutic agent, such as tamoxifen; and (b) the potential magnitude of beneficial response to chemotherapy.

DESCRIPTION OF THE RELATED ART

Gene Expression Studies

Oncologists have a number of treatment options available to them, including different combinations of chemotherapeutic drugs that are characterized as "standard of care," and a number of drugs that do not carry a label claim for the treatment of a particular cancer, but for which there is evidence of efficacy in that cancer. Best likelihood of good treatment outcome requires that patients at highest risk of metastatic disease be identified and assigned to optimal available cancer treatment. In particular, it is important to determine the likelihood of patient response to "standard of care" therapeutic drugs, such as cyclophosphamide, methotrexate, 5-fluorouracil, anthracyclines, taxanes, and anti-estrogen drugs, such as tamoxifen, because these have limited efficacy and a spectrum of often severe side effects. The identification of patients who are most or least likely to need and respond to available drugs thus could increase the net benefit these drugs have to offer, and decrease net morbidity and toxicity, via more intelligent patient selection.

Currently, diagnostic tests used in clinical practice are single analyte, and therefore do not capture the potential value of knowing relationships between dozens of different markers. Moreover, diagnostic tests are often based on immunohistochemistry, which is not quantitative. Immunohistochemistry often yields different results in different laboratories, in part because the reagents are not standardized, and in part because the interpretations are subjective. RNA-based tests, while potentially highly quantitative, have not been used because of the perception that RNA is destroyed in tumor specimens as routinely prepared, namely fixed in formalin and embedded in paraffin (FPE), and because it is inconvenient to obtain and store fresh tissue samples from patients for analysis.

Over the last two decades molecular biology and biochemistry have revealed hundreds of genes whose activities influence the behavior of tumor cells, their state of differentiation, and their sensitivity or resistance to certain therapeutic drugs. However, with a few exceptions, the status of these genes has not been exploited for the purpose of routinely making clinical decisions about drug treatments. In the last few years, several groups have published studies concerning the classification of various cancer types by microarray gene expression analysis of thousands of genes (see, e.g. Golub et al., *Science* 286:531-537 (1999); Bhattacharjae et al., Proc. Natl. Acad. Sci. USA 98:13790-13795 (2001); Chen-Hsiang et al., *Bioinformatics* 17 (Suppl. 1):S316-S322 (2001); Ramaswamy et al., *Proc. Natl. Acad. Sci. USA* 98:15149-15154 (2001); Martin et al., *Cancer Res.* 60:2232-2238 (2000); West et al., *Proc. Natl. Acad. Sci. USA* 98:11462-114 (2001); Sorlie et al., *Proc. Natl. Acad. Sci. USA* 98:10869-10874 (2001); Yan et al., *Cancer Res.* 61:8375-8380 (2001)). However, these studies have not yet yielded tests routinely used in clinical practice, in large part because microarrays require fresh or frozen tissue RNA and such specimens are not present in sufficient quantity to permit clinical validation of identified molecular signatures.

In the past three years, it has become possible to profile gene expression of hundreds of genes in formalin-fixed paraffin-embedded (FPE) tissue using RT-PCR technology. Methods have been described that are highly sensitive, precise, and reproducible (Cronin et al., *Am. J. Pathol.* 164:35-42 (2004)). Because thousands of archived FPE clinical tissue specimens exist with associated clinical records, such as survival, drug treatment history, etc., the ability to now quantitatively assay gene expression in this type of tissue enables rapid clinical studies relating expression of certain genes to patient prognosis and likelihood of response to treatments. Using data generated by past clinical studies allows for rapid results because the clinical events are historical. In contrast, for example, if one wished to carry out a survival study on newly recruited cancer patients one would generally need to wait for many years for statistically sufficient numbers of deaths to have occurred.

Breast Cancer Prognosis and Prediction

Breast cancer is the most common type of cancer among women in the United States, and is the leading cause of cancer deaths among women ages 40-59.

Currently only a few molecular tests are routinely used clinically in breast cancer. Immunohistochemical assays for estrogen receptor (ESR1) and progesterone receptor (PGR) proteins are used as a basis for selection of patients to treatment with anti-estrogen drugs, such as tamoxifen (TAM). In addition, ErbB2 (Her2) immunochemistry or fluorescence in situ hybridization (which measure protein and DNA, respectively) are used to select patients with the Her2 antagonist drugs, such as trastuzumab (Herceptin®; Genentech, Inc., South San Francisco, Calif.).

Because current tests for prognosis and for prediction of response to chemotherapy are inadequate, breast cancer treatment strategies vary between oncologists (Schott and Hayes, *J. Clin. Oncol.* PMID 15505274 (2004); Hayes, *Breast* 12:543-9 (2003)). Generally, lymph node negative patients whose tumors are found to be ESR1 positive are treated with an anti-estrogen drug, such as TAM, and patients whose tumors are found to be ESR1 negative are treated with chemotherapy. Often, ESR1 positive patients are also prescribed chemotherapy in addition to anti-estrogen therapy, accepting the toxic side effects of chemotherapy in order to modestly decrease the risk of cancer recurrence. Toxicities include, neuropathy, nausea and other gastrointestinal symptoms, hair loss and cognitive impairment. Recurrence is to be feared because recurrent breast cancer is usually metastatic and poorly responsive to treatment. Clearly, a need exists to identify those patients who are at substantial risk of recurrence (i.e., to provide prognostic information) and likely to respond to chemotherapy (i.e., to provide predictive information).

Likewise, a need exists to identify those patients who do not have a significant risk of recurrence, or who are unlikely to respond to chemotherapy, as these patients should be spared needless exposure to these toxic drugs.

Prognostic factors differ from treatment predictive factors in breast cancer. Prognostic factors are those variables related to the natural history of breast cancer, which influence the recurrence rates and outcome of patients once they have developed breast cancer. Clinical parameters that have been associated with a worse prognosis include, for example, lymph node involvement, increasing tumor size, and high grade tumors. Prognostic factors are frequently used to categorize patients into subgroups with different baseline relapse risks. In contrast, treatment predictive factors are variables related to the likelihood of an individual patient's beneficial response to a treatment, such as anti-estrogen or chemotherapy, independent of prognosis.

There is a great need for accurate, quantitative prognostic and predictive factors that can assist the practicing physician to make intelligent treatment choices, adapted to a particular patient's needs, based on well founded risk-benefit analysis.

SUMMARY OF THE INVENTION

In one aspect, the invention concerns a method for the prognosis of disease outcome in a breast cancer patient, comprising (a) quantitatively determining, in a biological sample comprising cancer cells obtained from the patient, the value of one or more of the following variables:
  (i) Proliferation Group Score;
  (ii) Invasion Group Score;
  (iii) Proliferation Group Threshold Score; and
  (iv) the expression levels of the RNA transcripts of one or more of the following individual genes CCNB1, BIRC5, MYBL2, PGR, STK6, MKI67, GSTM1, GAPD, RPLPO, and MMP11, or their expression products; wherein (b1) for every unit of an increase in the value of one or more of (i)-(iii) and/or of the RNA transcript(s) of one or more of the individual genes CCNB1, BIRC5, MYBL2, STK6, MKI67, GAPD, and MMP11, or the corresponding expression product(s), the patient is identified to have a proportionately increased risk of poor disease outcome; and (b2) for every unit of increased expression level(s) of the RNA transcript(s) of one or more of the individual genes PGR, GSTM1, and RPLPO, or the corresponding expression product(s), the patient is identified to have a proportionately decreased risk of poor disease outcome,
  wherein
  Proliferation Group Score=(BIRC5+MKI67+MYBL2+CCNB1+STK6)/5;
  Invasion Group Score=(CTSL2+MMP11)/2;
  Proliferation Group Threshold Score equals 6.5 if the Proliferation Group Score is less than 6.5; and is identical with the Proliferation Group Score, if the Proliferation Group Score is 6.5 or more, wherein
  the gene symbols in the equations represent the expression levels of the RNA transcripts of the respective genes, or their expression products; and
  wherein every individual gene or gene present in any of the variables can be substituted by another gene that coexpresses with said gene in said cancer with a Pearson's coefficient of $\geq 0.5$.

The patient can be a mammal, including higher primates, such as humans, and is preferably a human patient.

Disease outcome can be expressed in various forms, including overall patient survival, recurrence-free survival, or distant recurrence-free survival.

In a particular embodiment, the prognosis assumes that the patient receives no further treatment after surgical resection of said breast cancer.

In another embodiment, the expression levels are normalized relative to the expression levels of one or more reference genes, or their expression products, where the reference genes may be selected, for example, from the group consisting of ACTB, GAPD, GUS, RPLPO, and TFRC.

In yet another embodiment, the expression levels are normalized relative to the mean of the expression levels of ACTB, GAPD, GUS, RPLPO, and TFRC.

In a specific embodiment, the quantitative value of said disease outcome is directly proportionate with the value of the variable or variables determined over a continuum.

In further embodiments, the method comprises the determination of the Proliferation Score, and optionally one or both of the Proliferation Group Threshold Score and the Invasion Group Score.

The method of the invention may comprise determination of the expression levels of at least two, or at least three, or at least four, or at least five, or at least six, or at least seven, or at least eight of the individual genes listed in (iv), or their expression products.

In a specific embodiment, the method comprises determination of the expression levels of all individual genes listed in (iv), or their expression products.

The breast cancer may, for example, be lymph node negative and/or ESR1 positive.

The method of the present invention can be performed more than once on the same patient, such as, prior to and following chemotherapy, hormonal therapy and/or radiation therapy.

If the patient is determined to have an increased risk of poor disease outcome, it can be treated with chemotherapy, hormonal therapy and/or radiation therapy, following such determination, where chemotherapy includes all chemotherapy approaches used in clinical practice, including adjuvant and neoadjuvant chemotherapy.

In a particular embodiment, the chemotherapy comprises the administration of a taxane derivative, e.g. docetaxel or paclitaxel.

In another embodiment, the chemotherapy comprises the administration of an anthracycline derivative, e.g. doxorubicin.

In yet another embodiment, the chemotherapy comprises the administration of a topoisomerase inhibitor, e.g. camptothecin, topotecan, irinotecan, 20-S-camptothecin, 9-nitro-camptothecin, 9-amino-camptothecin, or GI147211.

In a further embodiment, the hormonal therapy comprises the administration of TAM.

In yet another embodiment, the hormonal therapy comprises the administration of an anti-estrogen drug, which may be an antagonist of estrogen binding to the estrogen receptor, or an inhibitor of estrogen biosynthesis, such as an aromatase inhibitor. Specific representatives of such anti-estrogen drugs include toremifene, anastrozole, and megasterol acetate.

The biological sample assayed by the methods of the present invention can be a sample from a solid tumor, i.e. a tissue sample comprising cancer cells.

The tissue may, for example, be fixed, paraffin-embedded, or fresh, or frozen, and can derive from fine needle, core, or other types of biopsy. In particular embodiments, the tissue sample is obtained by fine needle aspiration, bronchial lavage, or transbronchial biopsy.

In a further embodiment, the gene expression levels are determined by quantitative RT-PCR.

In yet another embodiment, the expression level of the expression product or products is determined by immunohistochemistry or by proteomics techniques.

In a still further embodiment, the method of the invention further comprises the step of creating a report summarizing the prognosis.

In another aspect, the invention concerns a method for quantitative determination of the likelihood of a beneficial response of an ESR1 positive breast cancer patient to treatment with an anti-estrogen drug, comprising quantitatively determining, in a biological sample comprising cancer cells obtained from said patient, one or more of the following variables:

(i) ESR1 Group Score; and (ii) the expression levels of the RNA transcripts of one or more of the following individual genes ESR1, SCUBE2, TFRC, and BCL2, or their expression products; wherein for every unit of increased numerical value of ESR1 Group Score, ESR1, SCUBE2, or BCL2 the patient is identified to have a proportionately increased likelihood of a beneficial response to treatment with an anti-estrogen drug, and for every unit of increased numerical value of TFRC the patient is identified as having a decreased likelihood of beneficial response to treatment with an anti-estrogen drug.

In one embodiment, the ESR1 Group Score, or the expression level of the ESR1 gene or its expression product is determined.

In another embodiment, the expression level of the ESR1 gene or its expression product is determined.

The anti-estrogen drug may, for example, be selected from the group consisting of tamixofen, toremifene, anastrozole, and megasterol acetate.

In another embodiment, the anti-estrogen drug is TAM.

The treatment predictive method of the present invention may comprising the step of preparing a report for the patient, including a treatment recommendation.

In a further embodiment, anti-estrogen drug treatment without chemotherapy is recommended when ESR1 expression for the patient is higher than the expression value measured in the same test for percentage of ER-positive, node-negative breast cancer patients, and the patient is otherwise known to be in a low risk group.

In another embodiment, the variable is the expression level of the RNA transcript of ESR1, or its expression product.

In a further embodiment, the method includes the step of determining the Recurrence Score for the patient.

In a particular embodiment, after determining the Recurrence Score, a treatment comprising chemotherapy is recommended when ESR1 expression for the patient is non-zero but is lower than the expression value measured in the same test for a particular percentage of ER-positive, node-negative breast cancer patients and the patient is otherwise known to be in a group having a high risk of recurrence.

In yet another aspect, the invention concerns a kit comprising a set of gene specific probes and/or primers for quantifying the expression of one or more of the genes listed in Table 1 by quantitative RT-PCR.

In a particular embodiment, the gene specific probes are selected from the group consisting of the probes listed in Table 7.

In another embodiment, the gene specific primers are selected from the group consisting of the forward and reverse primers listed in Table 7.

In yet another embodiment, the amplicon amplified by the quantitative RT-PCR is selected from the amplicons listed in Table 8.

In further embodiments, the kits of the present invention may comprise one or more reagents for expression of RNA from tumor samples, and/or one or more, where the containers may, for example, comprise pre-fabricated microarrays, a buffers, nucleotide triphosphates, reverse transcriptase, DNA polymerase, RNA polymerase, probes, or primers. The kit may additionally comprise a label or package insert with instructions for use of its components, such as, for example, for use in the prediction or prognosis of breast cancer.

DETAILED DESCRIPTION OF THE PREFERRED EMBODIMENT

A. Definitions

Figure 1:
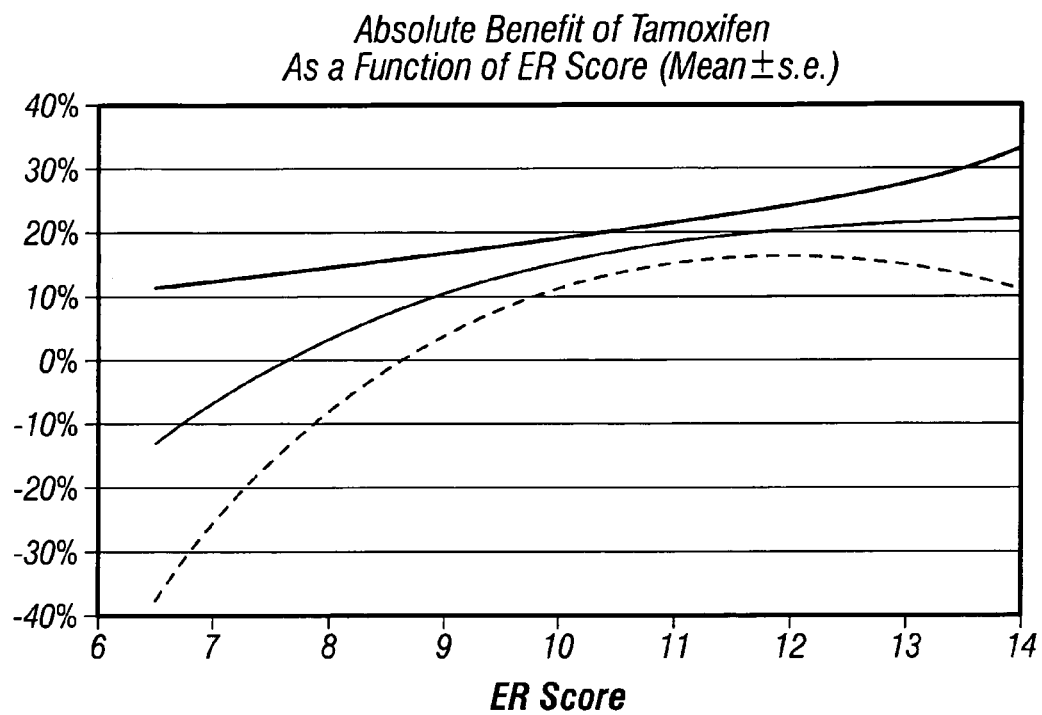
FIG. 1 shows the absolute increase in proportion of TAM treated patients who are distant disease-free at 10 years as a function of quantitative measurement of ESR1

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994); and Webster's New World™ Medical Dictionary, 2nd Edition, Wiley Publishing Inc., 2003, provide one skilled in the art with a general guide to many of the terms used in the present application. For purposes of the present invention, the following terms are defined below.

The term "beneficial response" means an improvement in any measure of patient status, including those measures ordinarily used in the art, such as overall survival, progression free survival, recurrence-free survival, and distant recurrence-free survival. Recurrence-free survival (RFS) refers to the time (in years) from surgery to the first local, regional, or distant recurrence. Distant recurrence-free survival (DFRS) refers to the time (in years) from surgery to the first anatomically distant recurrence. The calculation of these measures in practice may vary from study to study depending on the definition of events to be either censored or not considered.

The term "microarray" refers to an ordered arrangement of hybridizable array elements, preferably polynucleotide probes, on a substrate.

The term "polynucleotide," when used in singular or plural, generally refers to any polyribonucleotide or polydeoxribonucleotide, which may be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" specifically includes cDNAs. The term includes DNAs (including cDNAs) and RNAs that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritiated bases, are included within the term "polynucleotides" as defined herein. In general, the term "polynucleotide" embraces all chemically, enzymatically and/or metabolically modified forms of unmodified polynucleotides, as well as the chemical forms of DNA and RNA characteristic of viruses and cells, including simple and complex cells.

The term "oligonucleotide" refers to a relatively short polynucleotide, including, without limitation, single-stranded deoxyribonucleotides, single- or double-stranded ribonucleotides, RNA:DNA hybrids and double-stranded DNAs. Oligonucleotides, such as single-stranded DNA probe oligonucleotides, are often synthesized by chemical methods, for example using automated oligonucleotide synthesizers that are commercially available. However, oligonucleotides can be made by a variety of other methods, including in vitro recombinant DNA-mediated techniques and by expression of DNAs in cells and organisms.

The term "gene expression" describes the conversion of the DNA gene sequence information into transcribed RNA (the initial unspliced RNA transcript or the mature mRNA) or the encoded protein product. Gene expression can be monitored by measuring the levels of either the entire RNA or protein products of the gene or subsequences.

The phrase "gene amplification" refers to a process by which multiple copies of a gene or gene fragment are formed in a particular cell or cell line. The duplicated region (a stretch of amplified DNA) is often referred to as "amplicon." Often, the amount of the messenger RNA (mRNA) produced, i.e., the level of gene expression, also increases in the proportion of the number of copies made of the particular gene expressed.

Prognostic factors are those variables related to the natural history of breast cancer, which influence the recurrence rates and outcome of patients once they have developed breast cancer. Clinical parameters that have been associated with a worse prognosis include, for example, lymph node involvement, increasing tumor size, and high grade tumors. Prognostic factors are frequently used to categorize patients into subgroups with different baseline relapse risks. In contrast, treatment predictive factors are variables related to the likelihood of an individual patient's beneficial response to a treatment, such as anti-estrogen or chemotherapy, independent of prognosis.

The term "prognosis" is used herein to refer to the likelihood of cancer-attributable death or cancer progression, including recurrence and metastatic spread of a neoplastic disease, such as breast cancer, during the natural history of the disease. Prognostic factors are those variables related to the natural history of a neoplastic diseases, such as breast cancer, which influence the recurrence rates and disease outcome once the patient developed the neoplastic disease, such as breast cancer. In this context, "natural outcome" means outcome in the absence of further treatment. For example, in the case of breast cancer, "natural outcome" means outcome following surgical resection of the tumor, in the absence of further treatment (such as, chemotherapy or radiation treatment). Prognostic factors are frequently used to categorize patients into subgroups with different baseline risks, such as baseline relapse risks.

The term "prediction" is used herein to refer to the likelihood that a patient will respond either favorably or unfavorably to a drug or set of drugs, and also the extent of those responses. Thus, treatment predictive factors are those variables related to the response of an individual patient to a specific treatment, independent of prognosis. The predictive methods of the present invention can be used clinically to make treatment decisions by choosing the most appropriate treatment modalities for any particular patient. The predictive methods of the present invention are valuable tools in predicting if a patient is likely to respond favorably to a treatment regimen, such as anti-estrogen therapy, such as TAM treatment alone or in combination with chemotherapy and/or radiation therapy.

The term "long-term" survival is used herein to refer to survival for at least 3 years, more preferably for at least 8 years, most preferably for at least 10 years following surgery or other treatment.

The term "tumor," as used herein, refers to all neoplastic cell growth and proliferation, whether malignant or benign, and all pre-cancerous and cancerous cells and tissues.

The terms "cancer" and "cancerous" refer to or describe the physiological condition in mammals that is typically characterized by unregulated cell growth. Examples of cancer include, but are not limited to, breast cancer, ovarian cancer, colon cancer, lung cancer, prostate cancer, hepatocellular cancer, gastric cancer, pancreatic cancer, cervical cancer, liver cancer, bladder cancer, cancer of the urinary tract, thyroid cancer, renal cancer, carcinoma, melanoma, and brain cancer.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

In the context of the present invention, reference to "at least one," "at least two," "at least three," "at least four," "at least five," etc. of the genes listed in any particular gene set means any one or any and all combinations of the genes listed.

The term "node negative" cancer, such as "node negative" breast cancer, is used herein to refer to cancer that has not spread to the lymph nodes.

The terms "splicing" and "RNA splicing" are used interchangeably and refer to RNA processing that removes introns and joins exons to produce mature mRNA with continuous coding sequence that moves into the cytoplasm of an eukaryotic cell.

In theory, the term "exon" refers to any segment of an interrupted gene that is represented in the mature RNA product (B. Lewin. *Genes IV* Cell Press, Cambridge Mass. 1990). In theory the term "intron" refers to any segment of DNA that is transcribed but removed from within the transcript by splicing together the exons on either side of it. Operationally, exon sequences occur in the mRNA sequence of a gene as defined by Ref. SEQ ID numbers. Operationally, intron sequences are the intervening sequences within the genomic DNA of a gene, bracketed by exon sequences and having GT and AG splice consensus sequences at their 5' and 3' boundaries.

B. Detailed Description

The practice of the present invention will employ, unless otherwise indicated, conventional techniques of molecular biology (including recombinant techniques), microbiology, cell biology, and biochemistry, which are within the skill of the art. Such techniques are explained fully in the literature, such as, "Molecular Cloning: A Laboratory Manual", $2^{nd}$ edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology", $4^{th}$ edition (D. M. Weir & C. C. Blackwell, eds., Blackwell Science Inc., 1987); "Gene Transfer Vectors for Mammalian Cells" (J. M. Miller & M. P. Calos, eds., 1987); "Current Protocols in Molecular Biology" (F. M. Ausubel et al., eds., 1987); and "PCR: The Polymerase Chain Reaction", (Mullis et al., eds., 1994).

B.1. General Description of the Invention

Over the past two years Genomic Health, Inc and collaborators (Esteban et al., *Proc Am Soc Clin Oncol* 22: page 850, 2003 (abstract 3416); Cobleigh et al. *Soc Clin Oncol* 22: page 850, 2003 (abstract 3415); Soule et al., *Proc Am Soc Clin Oncol* 22: page 862, 2003 (abstract 3466)) reported several exploratory clinical studies of gene expression in early breast cancer, aimed at finding a molecular signature for recurrence risk. These studies used quantitative RT-PCR to test 250 candidate gene markers in frozen, paraffin-embedded (FPE) tissue specimens having linked clinical records. Analysis across all three studies was performed in order to examine whether genes could be identified which were consistently related to the risk of recurrence across a diverse group of patients. Based on these univariate results, multi-gene models were designed and analyzed across the three studies. A single multi-gene assay, consisting of 16 cancer-related genes and 5 reference genes, was developed to be tested prospectively in clinical validation studies. An algorithm called Recurrence Score (RS) was generated, which utilizes the measurements of these 21 mRNA species and reads out recurrence risk on a 100 point scale.

To test the clinical validity of this Recurrence Score test and algorithm, a blinded clinical trial with prospectively identified endpoints was carried out. This validation trial focused on patients treated with TAM alone in the randomized and registration arms of the National Surgical Adjuvant Breast and Bowel Project (NSABP) Study B-14 clinical trial population (Fisher B, Costantino J P, Redmond C K, et al: Endometrial cancer in TAM-treated breast cancer patients: Findings from the National Surgical Adjuvant Breast and Bowel Project (NSABP) B-14. *J Natl Cancer Inst* 86:527-537 (1994)). Genomic Health, Inc. and the NSABP carried out the 21 gene RT-PCR assay on 668 breast cancer tissue specimens derived from these patients and calculated a Recurrence Score for each patient.

Pre-specified cut-off points of Recurrence Score classified patients into one of three categories: low risk, intermediate risk, and high risk of distant disease recurrence. The proportion of the 668 patients categorized as low, intermediate, and high risk by the RT-PCR assay were 51%, 23%, and 27%, respectively. The Kaplan-Meier estimates and 95% confidence intervals for the rates of distant recurrence at 10 years were 6.8% (4.0%, 9.6%), 14.3% (8.3%, 20.3%) 30.5% (23.6%, 37.4%), respectively, for the low, intermediate, and high risk groups; the rate for the low risk group was significantly lower than the rate for the high risk group ($p<0.001$). In a multivariate Cox model relating distant recurrence to Recurrence Score, age, and tumor size, Recurrence Score provides significant ($p<0.001$) predictive power that goes beyond age and tumor size. This study validated the Recurrence Score as a powerful predictor of distant recurrence in patients without involved nodes who have tumors that are ESR1 positive and treated with TAM (Paik et al. Breast Cancer Research and Treatment 82, Supplement 1: page S10, 2003 (Abstract 16).

The invention disclosed herein derives, in part, from study of patients in the placebo arm of the NSABP B-14 clinical study (B-14) and, in part, from comparison of patients in the B-14 placebo arm to TAM-treated patients with patients in the randomized and registration arms of NSABP Study B-14. Breast cancer tissue derived from placebo-treated patients was quantitatively analyzed, using a RT-PCR assay to quantify the expression of sixteen cancer-related genes and five reference genes.

The quantitative gene expression analysis resulted in the identification of molecular indicators of prognosis. Based on analysis of the relationship between gene expression and distant recurrence-free survival in the placebo arm of the NSABP B-14 trial, a set of genes has been identified, the expression levels of which are indicative of outcome if no further treatment is provided to the patient. Outcome may be manifest in various measurements including survival, recurrence-free survival and distant recurrence-free survival, all of which are within the scope of the invention.

The prognostic genes and gene groups identified may be used singly or in particular combinations to predict outcome likelihood for particular patients. Prognostic indicators include, specifically, the proliferation group (BIRC5+MKI+MYBL2+CCNB1+STK6), the invasion group (CTSL2+MMP11), and one or more of the individual genes: CCNB1, BIRC5, MYBL2, PGR, STK6, MKI, GSTM1, GAPD, RPLP0, and MMP11.

In another aspect, the gene expression analysis disclosed herein resulted in the identification of molecular indicators of beneficial response to anti-estrogen drugs, such as TAM, based on analysis of the relationship between gene expression and distant recurrence-free survival in untreated patients from the placebo arm of B-14 as well as TAM treated patients from both registration and randomization arms of B-14.

Based on interaction analysis of the relationship between gene expression and distant recurrence-free survival in the combined placebo and treatment cohorts, a set of genes and gene groups has been identified, the expression levels of which are indicative of beneficial response to treatment TAM. These genes and gene groups may be used singly or in particular combinations to predict likelihood of beneficial response to treatment with TAM, or another anti-estrogen drug, for individual patients. Specifically, these genes/gene groups are: the ESR1 group (ESR1+PGR+BCL2+SCUBE2) and one or more of the individual genes ESR1, SCUBE2, TFRC, and BCL2.

A significant finding of the invention is that quantitative levels of ESR1 relate to likelihood of TAM benefit as a continuous variable across a 14 point expression scale. Thus, for an individual patient it is possible to provide a quantitative estimate of likelihood of benefit for this therapeutic agent, with higher ESR1 gene expression levels correlating with a greater chance of response. This information can be utilized in several ways. It provides a more refined assessment of the probability of a beneficial response to TAM treatment, and other anti-estrogen therapies, than has been available previously. TAM has significant side effects, including development of uterine cancer, deep vein thrombosis, pulmonary embolism, and cataracts (Physicians Desk Reference 2002). Similarly, other anti-estrogen drugs, such as, toremifene (Fareston®, Orion, Corp.), anastrozole (Arimidex®, AstraZeneca Pharmaceuticals), and megasterol acetate, have serious side-effects. As a result of the present invention, patients and their oncologists can now use the ESR1 score to assess risk versus benefit when deciding whether TAM treatment, or other anti-estrogen therapy, is appropriate.

While expression of ESR1 (principally as determined by immunochemistry measurement at the protein level) is routinely used in clinical practice to determine whether a patient should be treated with TAM, based on "ESR1 positive" or "ESR1 negative" status, the findings underlying the present invention relate to patients who are already defined as "ESR1 positive" by the conventional criteria. According to the present invention, it is possible to determine the likelihood of a beneficial response to TAM treatment, or treatment with other anti-estrogen drugs, among this group of patients.

ESR1 levels can be used in conjunction with the Recurrence Score (discussed below) to determine whether individual patients should be prescribed TAM (or another anti-estrogen drug) alone, or TAM (or another anti-estrogen drug) plus chemotherapy.

The invention additionally allows the design of a particular test, an example of which is given in the Example below, with precise ESR1 expression cut points that predict a high, intermediate of low level of benefit from TAM treatment, or treatment with other anti-estrogen drugs.

In various embodiments of the inventions, various technological approaches are available for determination of expression levels of the disclosed genes, including, without limitation, RT-PCR, microarrays, serial analysis of gene expression (SAGE) and Gene Expression Analysis by Massively Parallel Signature Sequencing (MPSS), which will be discussed in detail below. In particular embodiments, the expression level of each gene may be determined in relation to various features of the expression products of the gene including exons, introns, protein epitopes and protein activity.

B.2 Gene Expression Profiling

In general, methods of gene expression profiling can be divided into two large groups: methods based on hybridization analysis of polynucleotides, and methods based on sequencing of polynucleotides. The most commonly used methods known in the art for the quantification of mRNA expression in a sample include northern blotting and in situ hybridization (Parker & Barnes, *Methods in Molecular Biology* 106:247-283 (1999)); RNAse protection assays (Hod, *Biotechniques* 13:852-854 (1992)); and reverse transcription polymerase chain reaction (RT-PCR) (Weis et al., *Trends in Genetics* 8:263-264 (1992)). Alternatively, antibodies may be employed that can recognize specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), and gene expression analysis by massively parallel signature sequencing (MPSS).

Two biological processes commonly involved in tumorigenesis include gene amplification and DNA methylation. Both processes result in the abnormal expression of genes important in tumor formation or progression. Methods that monitor gene amplification and DNA methylation can therefore be considered surrogate methods for gene expression profiling.

Gene amplification is a common alteration in many cancers that can lead to elevated expression of cellular oncogenes (Meltzer, P. et al., Cancer Genet Cytogenet. 19:93 (1986). In breast cancer, there is good correlation between ERBB2 gene amplification and ERBB2 overexpression (Nagai, M. A. et al., Cancer Biother 8:29 (1993), Savinainen, K. J. et al., Am. J. Pathol. 160:339 (2002)). Amplification of the ERBB2 gene, leading to its overexpression, correlates with poor prognosis (Press, M. F. et al., J. Clin. Oncol. 15:2894 (1997), Slamon, D. J. et al., Science 244:707 (1989)) and is predictive for response to anti-HER2 therapy in combination with standard chemotherapy (Seidman, A. D. et al., J. Clin. Oncol. 19:1866 (2001)).

DNA methylation has also been shown to be a common alteration in cancer leading to elevated or decreased expression of a broad spectrum of genes (Jones, P. A. Cancer Res. 65:2463 (1996)). In general, hypomethylation of CpG islands in the promoter regions and regulatory elements results in increased gene expression, including many oncogenes (Hanada, M., et al., Blood 82:1820 (1993), Feinberg, A. P. and Vogelstein, B. Nature 301:89 (1983)). Because DNA methylation correlates with the level of specific gene expression in many cancers, it serves as a useful surrogate to expression profiling of tumors (Toyota, M. et al., Blood 97: 2823 (2001), Adorjan, P. et al. Nucl. Acids. Res. 10:e21 (2002)).

a. Reverse Transcriptase PCR (RT-PCR)

Of the techniques listed above, the most sensitive and most flexible quantitative method is RT-PCR, which can be used to compare mRNA levels in different sample populations, in normal and tumor tissues, with or without drug treatment, to characterize patterns of gene expression, to discriminate between closely related mRNAs, and to analyze RNA structure.

The first step is the isolation of mRNA from a target sample. The starting material is typically total RNA isolated from human tumors or tumor cell lines, and corresponding normal tissues or cell lines, respectively. Thus RNA can be isolated from a variety of primary tumors, including breast, lung, colon, prostate, brain, liver, kidney, pancreas, spleen, thymus, testis, ovary, uterus, etc., tumor, or tumor cell lines, with pooled DNA from healthy donors. If the source of mRNA is a primary tumor, mRNA can be extracted, for example, from frozen or archived paraffin-embedded and fixed (e.g. formalin-fixed) tissue samples.

General methods for mRNA extraction are well known in the art and are disclosed in standard textbooks of molecular biology, including Ausubel et al., *Current Protocols of Molecular Biology*, John Wiley and Sons (1997). Methods for RNA extraction from paraffin embedded tissues are disclosed, for example, in Rupp and Locker, *Lab Invest.* 56:A (1987), and De Andrés et al., *BioTechniques* 18:42044 (1995). In particular, RNA isolation can be performed using purification kit, buffer set and protease from commercial manufacturers, such as Qiagen, according to the manufacturer's instructions. For example, total RNA from cells in culture can be isolated using Qiagen RNeasy mini-columns. Other commercially available RNA isolation kits include Master-Pure™ Complete DNA and RNA Purification Kit (EPICENTRE®, Madison, Wis.), and Paraffin Block RNA Isolation Kit (Ambion, Inc.). Total RNA from tissue samples can be isolated using RNA Stat-60 (Tel-Test). RNA prepared from tumor can be isolated, for example, by cesium chloride density gradient centrifugation.

As RNA cannot serve as a template for PCR, the first step in gene expression profiling by RT-PCR is the reverse transcription of the RNA template into cDNA, followed by its exponential amplification in a PCR reaction. The two most commonly used reverse transcriptases are avilo myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, Calif., USA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3'-5' proofreading endonuclease activity. Thus, TaqMan® PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TaqMan® RT-PCR can be performed using commercially available equipment, such as, for example, ABI PRISM 7700™ Sequence Detection System™ (Perkin-Elmer-Applied Biosystems, Foster City, Calif., USA), or Lightcycler (Roche Molecular Biochemicals, Mannheim, Germany). In a preferred embodiment, the 5' nuclease procedure is run on a real-time quantitative PCR device such as the ABI PRISM 7700™ Sequence Detection System™. The system consists of a thermocycler, laser, charge-coupled device (CCD), camera and computer. The system amplifies samples in a 96-well format on a thermocycler. During amplification, laser-induced fluorescent signal is detected at the CCD. The system includes software for running the instrument and for analyzing the data.

5'-Nuclease assay data are initially expressed as $C_T$, or the threshold cycle. As discussed above, fluorescence values are recorded during every cycle and represent the amount of product amplified to that point in the amplification reaction. The point when the fluorescent signal is first recorded as statistically significant is the threshold cycle ($C_T$).

To minimize errors and the effect of sample-to-sample variation, RT-PCR is usually performed using one or more reference genes as internal standards. The ideal internal standard is expressed at a constant level among different tissues, and is unaffected by the experimental treatment. RNAs most frequently used to normalize patterns of gene expression are mRNAs for the housekeeping genes glyceraldehyde-3-phosphate-dehydrogenase (GAPD) and β-actin (ACTB).

A more recent variation of the RT-PCR technique is the real time quantitative PCR, which measures PCR product accumulation through a dual-labeled fluorigenic probe (i.e., TaqMan® probe). Real time PCR is compatible both with quantitative competitive PCR, where internal competitor for each target sequence is used for normalization, and with quantitative comparative PCR using a normalization gene contained within the sample, or a housekeeping gene for RT-PCR. For further details see, e.g. Held et al., *Genome Research* 6:986-994 (1996).

The steps of a representative protocol for profiling gene expression using fixed, paraffin-embedded tissues as the RNA source, including mRNA isolation, purification, primer extension and amplification are given in various published journal articles {for example: T. E. Godfrey et al. J. Molec. Diagnostics 2: 84-91 (2000); K. Specht et al., Am. J. Pathol. 158: 419-29 (2001); Cronin et al., Am J Pathol 164:35-42 (2004)}. Briefly, a representative process starts with cutting about 10 μm thick sections of paraffin-embedded tumor tissue samples. The RNA is then extracted, and protein and DNA are removed. After analysis of the RNA concentration, RNA repair and/or amplification steps may be included, if necessary, and RNA is reverse transcribed using gene specific promoters followed by RT-PCR.

b. Microarrays

Differential gene expression can also be identified, or confirmed using the microarray technique. Thus, the expression profile of breast cancer-associated genes can be measured in either fresh or paraffin-embedded tumor tissue, using microarray technology. In this method, polynucleotide sequences of interest (including cDNAs and oligonucleotides) are plated, or arrayed, on a microchip substrate. The arrayed sequences are then hybridized with specific DNA probes from cells or tissues of interest. Just as in the RT-PCR method, the source of mRNA typically is total RNA isolated from human tumors or tumor cell lines, and corresponding normal tissues or cell lines. Thus RNA can be isolated from a variety of primary tumors or tumor cell lines. If the source of mRNA is a primary tumor, mRNA can be extracted, for example, from frozen or archived paraffin-embedded and fixed (e.g. formalin-fixed) tissue samples, which are routinely prepared and preserved in everyday clinical practice.

In a specific embodiment of the microarray technique, PCR amplified inserts of cDNA clones are applied to a substrate in a dense array. Preferably at least 10,000 nucleotide sequences are applied to the substrate. The microarrayed genes, immobilized on the microchip at 10,000 elements each, are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy or by another detection method, such as a CCD camera. Quantitation of hybridization of each arrayed element allows for assessment of corresponding mRNA abundance. With dual color fluorescence, separately labeled cDNA probes generated from two sources of RNA are hybridized pairwise to the array. The relative abundance of the transcripts from the two sources corresponding to each specified gene is thus determined simultaneously. The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels (Schena et al., *Proc. Natl. Acad. Sci. USA* 93(2):106-149 (1996)). Microarray analysis can be performed by commercially available equipment, following manufacturer's protocols, such as by using the Affymetrix GenChip technology, or Incyte's microarray technology.

The development of microarray methods for large-scale analysis of gene expression makes it possible to search systematically for molecular markers of cancer classification and outcome prediction in a variety of tumor types.

c. Serial Analysis of Gene Expression (SAGE)

Serial analysis of gene expression (SAGE) is a method that allows the simultaneous and quantitative analysis of a large number of gene transcripts, without the need of providing an individual hybridization probe for each transcript. First, a short sequence tag (about 10-14 bp) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag. For more details see, e.g. Velculescu et al., *Science* 270:484-487 (1995); and Velculescu et al., *Cell* 88:243-51 (1997).

d. Gene Expression Analysis by Massively Parallel Signature Sequencing (MPSS)

This method, described by Brenner et al., *Nature Biotechnology* 18:630-634 (2000), is a sequencing approach that combines non-gel-based signature sequencing with in vitro cloning of millions of templates on separate 5 μm diameter microbeads. First, a microbead library of DNA templates is constructed by in vitro cloning. This is followed by the assembly of a planar array of the template-containing microbeads in a flow cell at a high density (typically greater than $3 \times 10^6$ microbeads/cm$^2$). The free ends of the cloned templates on each microbead are analyzed simultaneously, using a fluorescence-based signature sequencing method that does not require DNA fragment separation. This method has been shown to simultaneously and accurately provide, in a single operation, hundreds of thousands of gene signature sequences from a yeast cDNA library.

e. General Description of the mRNA Isolation, Purification and Amplification

The steps of a representative protocol for profiling gene expression using fixed, paraffin-embedded tissues as the RNA source, including mRNA isolation, purification, primer extension and amplification are provided in various published journal articles (for example: T. E. Godfrey et al,. *J. Molec. Diagnostics* 2: 84-91 [2000]; K. Specht et al., *Am. J. Pathol.* 158: 419-29 [2001]). Briefly, a representative process starts with cutting about 10 μm thick sections of paraffin-embedded tumor tissue samples. The RNA is then extracted, and protein and DNA are removed. After analysis of the RNA concentration, RNA repair and/or amplification steps may be included, if necessary, and RNA is reverse transcribed using gene specific promoters followed by RT-PCR. Finally, the data are analyzed to identify the best treatment option(s) available to the patient on the basis of the characteristic gene expression pattern identified in the tumor sample examined, dependent on the predicted likelihood of cancer recurrence.

f. Breast Cancer Gene Set, Assayed Gene Subsequences, and Clinical Application of Gene Expression Data An important aspect of the present invention is to use the measured expression of certain genes by breast cancer tissue to provide prognostic or predictive information. For this purpose it is necessary to correct for (normalize away) both differences in the amount of RNA assayed and variability in the quality of the RNA used. Therefore, the assay typically measures and incorporates the expression of certain normalizing genes, including well known housekeeping genes, such as β-actin, GAPD, GUS, RPLO, and TFRC, as shown in the Example below. Alternatively, normalization can be based on the mean or median signal ($C_T$) of all of the assayed genes or a large subset thereof (global normalization approach). Below, unless noted otherwise, gene expression means normalized expression.

g. Design of Intron-Based PCR Primers and Probes

According to one aspect of the present invention, PCR primers and probes are designed based upon intron sequences present in the gene to be amplified. Accordingly, the first step in the primer/probe design is the delineation of intron sequences within the genes. This can be done by publicly available software, such as the DNA BLAT software developed by Kent, W. J., *Genome Res.* 12(4):656-64 (2002), or by the BLAST software including its variations. Subsequent steps follow well established methods of PCR primer and probe design.

In order to avoid non-specific signals, it is important to mask repetitive sequences within the introns when designing the primers and probes. This can be easily accomplished by using the Repeat Masker program available on-line through the Baylor College of Medicine, which screens DNA sequences against a library of repetitive elements and returns a query sequence in which the repetitive elements are masked. The masked intron sequences can then be used to design primer and probe sequences using any commercially or otherwise publicly available primer/probe design packages, such as Primer Express (Applied Biosystems); MGB assay-by-design (Applied Biosystems); Primer3 (Steve Rozen and Helen J. Skaletsky (2000) Primer3 on the WWW for general users and for biologist programmers. In: Krawetz S, Misener S (eds) *Bioinformatics Methods and Protocols: Methods in Molecular Biology*. Humana Press, Totowa, N.J., pp 365-386).

The most important factors considered in PCR primer design include primer length, melting temperature (Tm), and G/C content, specificity, complementary primer sequences, and 3'-end sequence. In general, optimal PCR primers are generally 17-30 bases in length, and contain about 20-80%, such as, for example, about 50-60% G+C bases. Tm's between 50 and 80° C., e.g. about 50 to 70° C. are typically preferred.

For further guidelines for PCR primer and probe design see, e.g. Dieffenbach, C. W. et al., "General Concepts for PCR Primer Design" in: *PCR Primer, A Laboratory Manual*, Cold Spring Harbor Laboratory Press, New York, 1995, pp. 133-155; Innis and Gelfand, "Optimization of PCRs" in: *PCR Protocols, A Guide to Methods and Applications*, CRC Press, London, 1994, pp. 5-11; and Plasterer, T. N. Primerselect: Primer and probe design. *Methods Mol. Biol.* 70:520-527 (1997), the entire disclosures of which are hereby expressly incorporated by reference.

B.3 Algorithms and Statistical Methods

The present invention takes advantage of certain algorithms and statistical methods, which are described in copending application Ser. No. 10/883,303.

When quantitative RT-PCR (qRT-PCR) is used to measure mRNA levels, mRNA amounts are expressed in $C_T$ (threshold cycle) units (Held et al., *Genome Research* 6:986-994 (1996)). The averaged sum of reference mRNA $C_T$s is set as a fixed number such as zero, and each measured test mRNA $C_T$ is given relative to this fixed point. For example, if, for a certain patient tumor specimen the average of $C_T$s of the 5 reference genes found to be 31 and $C_T$ of the test gene X is found to be 35, the reported value for gene X is −4 (i.e. 31-35).

As a first step following the quantitative determination of mRNA levels, the genes identified in the tumor specimen and known to be associated with the molecular pathology of cancer are grouped into subsets. Thus, genes known to be associated with proliferation will constitute the "Proliferation Group" (axis, or subset). Genes known to be associated with invasion of cancer will constitute the "Invasion Group" (axis, or subset). Genes associated with key growth factor receptor pathway(s) will constitute the "Growth Factor Group" (axis, or subset), also referred to as GRB7 Group. Genes known to be involved with activating or signaling through the estrogen receptor (ESR1) will constitute the "Estrogen Receptor (ER) Group" (axis, or subset), and so on. This list of subsets is, of course, not limiting. The subsets (axes) created will depend on the particular cancer, i.e. breast, prostate, pancreatic, lung, etc. cancer. In general, genes the expression of which is known to correlate with each other, or which are known to be involved in the same pathway are grouped together.

In the next step, the measured tumor level of each mRNA in a subset is multiplied by a coefficient reflecting its relative intra-set contribution to the risk of cancer recurrence and this product is added to the other products between mRNA levels in the subset and their coefficients, to yield a term, e.g. a proliferation term, an invasion term, a growth factor term, etc. For example, in the case of lymph node-negative invasive breast cancer the growth factor term is (0.45 to 1.35)×GRB7+ (0.05 to 0.15)×ErbB2, such as, for example 0.9×GRB7+0.1× ERBB2 (see Example below).

The contribution of each term to the overall recurrence score is weighted by use of a coefficient. For example, in the case of lymph node-negative invasive breast cancer the coefficient of the growth factor term can be between 0.23 and 0.70.

Additionally, for some terms, such as the growth factor and proliferation terms, a further step is performed. If the relationship between the term and the risk of recurrence is non-linear, a non-linear functional transform of the term, such as a threshold is used Thus, in lymph node-negative invasive breast cancer, when the growth factor term is found at <8 the value is fixed at 8.

The sum of the terms obtained provides the recurrence score (RS), which predicts the likelihood of cancer recurrence in the normal course of the disease.

The RS scale generated by the algorithm of the present invention can be adjusted in various ways. Thus, the range could be selected such that the scale run from 0 to 10, 0 to 50, or 0 to 100, for example.

For example, in the particular scaling approach described in the Example below, scaled recurrence score is calculated on a scale of 0 to 100. For convenience, 10 $C_T$ units are added to each measured $C_T$ value, and unscaled RS is calculated as described before. Equations for calculating unscaled RS and scaled RS are provided in the following Example.

In calculating the Recurrence Score, or any variable used to calculate the Recurrence Score, any gene can be substituted by another gene that coexpresses in a set of at least 30 different patient specimens of that tumor type (such as breast cancer) with the first gene in the particular cancer tested with a Pearson's coefficient of $\geq 0.5$. Similarly, any individual gene, or gene within a gene group (subset) included in the prognostic and predictive methods of the present invention can be substituted by another gene that coexpresses with the first gene in the particular cancer tested with a Pearson's coefficient of $\geq 0.5$.

B.4 Anti-Estrogen Drug Treatment

Estrogen is known to promote the growth of some cancers, such as breast cancers, especially those that express the estrogen receptor (ESR1). Several therapies have been developed to block the effect of estrogen, or to lower estrogen levels in such patient, especially in ESR1 positive breast cancer patients.

Anti-estrogen drugs can be generally classified as either antagonists of estrogen binding to the estrogen receptor, or are inhibitors of estrogen biosynthesis, such as aromatase inhibitors.

The most commonly used anti-estrogen drug is TAM, which belong to the class of estrogen binding to the estrogen receptor, is typically taken orally, once a day for five years following surgical resection of breast cancer, and/or chemo- or radiation therapy. Clinical studies have shown that the use of TAM as an adjuvant therapy after surgery reduces the risk of cancer recurrence, however, the response of ESR1 positive patients to this treatment varies, and there have been no clear predictors of responsiveness available.

Other anti-estrogen drugs include raloxifene, which, like TAM, blocks the effect of estrogen on breast tissue and breast cancer; and toremifene citrate, which is closely related to TAM, and may be an option for post menopausal women with metastatic breast cancer.

Anastrozole, an aromatase inhibitor, acts by preventing estrogen from activating its receptor, blocking an enzyme needed for production of estrogen. Anastrozole is currently an option for women whose advanced breast cancer continues to grow during or after TAM treatment.

Megesterol acetate is typically used for hormonal treatment of advanced breast cancer, usually for women whose cancers fail to respond to TAM.

All treatments are limited by serious side effects, and by the lack of reliable predictors of patient response, which would enable a physician to make an intelligent risk-benefit analysis before recommending a particular treatment.

B.5 Cancer Chemotherapy

Chemotherapeutic agents used in cancer treatment can be divided into several groups, depending on their mechanism of action. Some chemotherapeutic agents directly damage DNA and RNA. By disrupting replication of the DNA such chemotherapeutics either completely halt replication, or result in the production of nonsense DNA or RNA. This category includes, for example, cisplatin (Platinol®), daunorubicin (Cerubidine®), doxorubicin (Adriamycin®), and etoposide (VePesid®). Another group of cancer chemotherapeutic agents interfere with the formation of nucleotides or deoxyribonucleotides, so that RNA synthesis and cell replication is blocked. Examples of drugs in this class include methotrexate (Abitrexate®), mercaptopurine (Purinethol®), fluorouracil (Adrucil®), and hydroxyurea (Hydrea®). A third class of chemotherapeutic agents effects the synthesis or breakdown of mitotic spindles, and, as a result, interrupt cell division. Examples of drugs in this class include Vinblastine (Velban®), Vincristine (Oncovin®) and taxanes, such as, Paci- taxel (Taxol®), and Tocetaxel (Taxotere®) Tocetaxel is currently approved in the United States to treat patients with locally advanced or metastatic breast cancer after failure of prior chemotherapy, and patients with locally advanced or metastatic non-small cell lung cancer after failure of prior platinum-based chemotherapy. The prediction of patient response to all of these, and other chemotherapeutic agents is specifically within the scope of the present invention.

In a specific embodiment, chemotherapy includes treatment with a taxane derivative. Taxanes include, without limitation, paclitaxel (Taxol®) and docetaxel (Taxotere®), which are widely used in the treatment of cancer. As discussed above, taxanes affect cell structures called microtubules, which play an important role in cell functions. In normal cell growth, microtubules are formed when a cell starts dividing.

Once the cell stops dividing, the microtubules are broken down or destroyed. Taxanes stop the microtubules from breaking down; which blocks cancer cell division.

In another specific embodiment, chemotherapy includes treatment with an anthracycline derivative, such as, for example, doxorubicin, daunorubicin, and aclacinomycin.

In a further specific embodiment, chemotherapy includes treatment with a topoisomerase inhibitor, such as, for example, camptothecin, topotecan, irinotecan, 20-S-camptothecin, 9-nitro-camptothecin, 9-amino-camptothecin, or GI147211.

Treatment with any combination of these and other chemotherapeutic drugs is specifically contemplated.

Most patients receive chemotherapy immediately following surgical removal of tumor. This approach is commonly referred to as adjuvant therapy. However, chemotherapy can be administered also before surgery, as so called neoadjuvant treatment. Although the use of neo-adjuvant chemotherapy originates from the treatment of advanced and inoperable breast cancer, it has gained acceptance in the treatment of other types of cancers as well. The efficacy of neoadjuvant chemotherapy has been tested in several clinical trials. In the multi-center National Surgical Adjuvant Breast and Bowel Project B-18 (NSAB B-18) trial (Fisher et al., *J. Clin. Oncology* 15:2002-2004 (1997); Fisher et al., *J. Clin. Oncology* 16:2672-2685 (1998)) neoadjuvant therapy was performed with a combination of adriamycin and cyclophosphamide ("AC regimen"). In another clinical trial, neoadjuvant therapy was administered using a combination of 5-fluorouracil, epirubicin and cyclophosphamide ("FEC regimen") (van Der Hage et al., *J. Clin. Oncol.* 19:4224-4237 (2001)). Newer clinical trials have also used taxane-containing neoadjuvant treatment regiments. See, e.g. Holmes et al., *J. Natl. Cancer Inst.* 83:1797-1805 (1991) and Molitemi et al., *Seminars in Oncology*, 24:S17-10-S-17-14 (1999). For further information about neoadjuvant chemotherapy for breast cancer see, Cleator et al., *Endocrine-Related Cancer* 9:183-195 (2002).

B.6 Kits of the Invention

The materials for use in the methods of the present invention are suited for preparation of kits produced in accordance with well known procedures. The invention thus provides kits comprising agents, which may include gene-specific or gene-selective probes and/or primers, for quantitating the expression of the disclosed genes for predicting prognostic outcome or response to treatment. Such kits may optionally contain reagents for the extraction of RNA from tumor samples, in particular fixed paraffin-embedded tissue samples and/or reagents for RNA amplification. In addition, the kits may optionally comprise the reagent(s) with an identifying description or label or instructions relating to their use in the methods of the present invention. The kits may comprise containers (including microtiter plates suitable for use in an automated implementation of the method), each with one or more of the various reagents (typically in concentrated form) utilized in the methods, including, for example, pre-fabricated microarrays, buffers, the appropriate nucleotide triphosphates (e.g., dATP, dCTP, dGTP and dTTP; or rATP, rCTP, rGTP and UTP), reverse transcriptase, DNA polymerase, RNA polymerase, and one or more probes and primers of the present invention (e.g., appropriate length poly(T) or random primers linked to a promoter reactive with the RNA polymerase). Mathematical algorithms used to estimate or quantify prognostic or predictive information are also properly potential components of kits.

The methods provided by the present invention may also be automated in whole or in part.

All aspects of the present invention may also be practiced such that a limited number of additional genes that are co-expressed with the disclosed genes, for example as evidenced by high Pearson correlation coefficients, are included in a prognostic or predictive test in addition to and/or in place of disclosed genes.

Having described the invention, the same will be more readily understood through reference to the following Example, which is provided by way of illustration, and is not intended to limit the invention in any way.

EXAMPLE

A study of the Relationship between Gene Expression and Prognosis and Likelihood of Beneficial Response to Tamoxifen in Early Breast Cancer Patients Methods This study employs tissue and data from NSABP Study B-14: "A Clinical Trial to Assess Tamoxifen in Patients with Primary Breast Cancer and Negative Axillary Nodes Whose Tumors are Positive for Estrogen Receptors." The results of this trial, conducted to evaluate the worth of postoperative tamoxifen therapy in women with ER-positive ($\geq$10 fmol/mg cytosol protein), invasive breast cancer and histologically negative axillary lymph nodes, were reported by Fisher B, Costantino JP, Redmond C K, et al: Endometrial cancer in TAM-treated breast cancer patients: Findings from the National Surgical Adjuvant Breast and Bowel Project (NSABP) B-14. J Natl Cancer Inst 86:527-537(1994).

1.1 Fixed paraffin-embedded breast tumor tissue samples from up to 450 patients, who were treated at study entry with placebo alone in the B-14 study, were analyzed. For each evaluable patient, the expression of 16 cancer-related genes and 5 reference genes was quantitatively assessed by RT-PCR. The relationship between disease recurrence and (a) recurrence score, (b) expression of genes in particular gene groups, or (c) expression of individual genes was evaluated.

1.2 Inclusion Criteria 1.2.1 Enrolled in NSABP Study B-14: "A Clinical Trial to Assess Tamoxifen in Patients with Primary Breast Cancer and Negative Axillary Nodes Whose Tumors are Positive for Estrogen Receptors."

1.2.2 Randomization to placebo or to TAM in the placebo-controlled part of the study.

1.2.3 Clinically eligible with follow-up 1.3 Exclusion Criteria 1.3.1 No tumor block available from initial diagnosis in the NSABP archive.

1.3.2 No tumor or very little tumor (Group 1) in block as assessed by examination of the H&E slide.

1.3.3 Insufficient RNA (<275 ng) for RT-PCR analysis.

1.3.4 Average non-normalized CT for the 5 reference genes >35.

1.4 Gene Panel 1.4.1 Analysis of 16 cancer-related genes and 5 reference genes listed in Table 1 was carried out using quantitative RT-PCR.

1.4.2 Patient Survival.

Distant recurrence-free survival (DRFS) is based on the time (in years) from surgery to first distant recurrence. Contralateral disease, other second primary cancers, and deaths prior to distant recurrence will be considered censoring events. For the primary analysis, ipsilateral breast recurrence, local chest wall recurrence and regional recurrence is ignored, i.e., not considered either as an event or a censoring event.

1.4.3 Gene Expression.

Expression levels of 21 genes listed in Table 1 were reported as values from the GHI assay. Gene expression values were normalized relative to the mean of the reference genes. For each cancer-related gene, cycle threshold ($C_T$) measurements were obtained by RT-PCR, and normalized relative to a set of five reference genes listed in Table 1. The reference genes are known to be relatively invariant in breast cancer as well as under various sample and process conditions, making them useful for normalizing for extraneous effects. Reference-normalized expression measurements typically range from 0 to 15, where a one unit increase generally reflects a 2-fold increase in RNA quantity.

1.4.4 Cancer-Related Genes and Reference Genes.

TABLE 1

Gene Expression Panel

| Cancer-Related Genes | Accession Number | Reference Genes | Accession Number |
|---|---|---|---|
| BAG1 | NM_004323 | ACTB | NM_001101 |
| BCL2 | NM_000633 | GAPD | NM_002046 |
| CCNB1 | NM_031966 | GUSB | NM_000181 |
| CD68 | NM_001251 | RPLP0 | NM_001002 |
| SCUBE2 | NM_020974 | TFRC | NM_003234 |
| CTSL2 | NM_001333 | | |
| ESR1 | NM_000125 | | |
| GRB7 | NM_005310 | | |
| GSTM1 | NM_000561 | | |
| ERBB2 | NM_004448 | | |
| MKI67 | NM_002417 | | |
| MYBL2 | NM_002466 | | |
| PGR | NM_000926 | | |
| STK6 | NM_003600 | | |
| MMP11 | NM_005940 | | |
| BIRC5 | NM_001168 | | |

1.4.5 Recurrence Score

The Recurrence Score (RS) on a scale from 0 to 100 is derived from the reference-normalized expression measurements as follows:

$RSu$(recurrence score unscaled) =

$0.47 \times GRB7$ Group Threshold Score −
$0.34 \times ESR1$ Group Score +
$1.04 \times$Proliferation Group Threshold Score +
$0.10 \times$Invasion Group Score +
$0.05 \times CD68 - 0.08 \times GSTM1 - 0.07 \times BAG1$ where:

$GRB7$ Group Score = $0.9 \times GRB7 + 0.1 \times ERBB2$ $GRB7$ Group Threshold Score =

$$\begin{cases} 8 & \text{If } GrB7 \text{ Group Score} < 8 \\ GRB7 \text{ Group Score} & \text{Otherwise} \end{cases}$$

$ESR1$ Group Score = $(ESR1 + PGR + BCL2 + SCUBE2)/4$

Proliferation Group Score =

$(BIRC5 + MKI67 + MYBL2 + CCNB1 + STK6)/5$

Proliferation Group Threshold Score =

$$\begin{cases} 6.5 & \text{If } Prolif. \text{ Group Score} < 6.5 \\ \text{Proliferation Group Score} & \text{Otherwise} \end{cases}$$

Invasion Group Score = $(CTSL2 + MMP11)/2$

The $RS_u$ (Recurrence Score unscaled) is then rescaled to be between 0 and 100:

$$RS = \begin{cases} 0 & \text{if } 20 \times (RS_U - 6.7) < 0 \\ 20 \times (RS_U - 6.7) & \text{if } 0 \leq 20 \times (RS_U - 6.7) \leq 100 \\ 100 & \text{if } 20 \times (RS_U - 6.7) > 100 \end{cases}$$

Based on a Cox proportional hazards model, the correlation between cancer recurrence and Recurrence Score was evaluated as a continuous variable. The evaluation additionally included the Proliferation Group, GRB7 Group, ESR1 Group, Invasion Group, and each of the sixteen cancer-related genes as continuous variables.

For the purpose of identifying prognostic genes, the primary objective was to explore the relation between gene expression and distant recurrence-free survival (DRFS) and overall survival (OS) in the untreated patient arm. DRFS was based on the time (in years) from surgery to first distant recurrence where contralateral disease, other second primary cancers, and deaths prior to distant recurrence were considered censoring events and ipsilateral breast recurrence, local chest wall recurrence and regional recurrences were ignored. Main effect Cox proportional hazard models (D. R. Cox (1972) Regression Models and Life-Tables (with discussion). *J Royal Statistical Soc.* B, 34:187-220) were utilized to compare the additional contribution of gene expression beyond standard clinical prognostics variables, including age, clinical tumor size, and tumor grade. A test for comparing the reduced model, excluding the gene expression variable, versus the competing full model including the gene variable of interest, called the likelihood ratio test (Ronald Fisher (1922) "On the Mathematical Foundations of Theoretical Statistics", *Phil. Trans. Royal Soc.*, series A, 222:326, 1922; Leonard Savage (1962), The Foundations of Statistical Inference (1962)) was utilized to identify statistically significant prognostic genes.

For the purpose of identifying treatment predictive genes in breast cancer, our primary objective was to explore the relation between gene expression and DRFS and OS in treated patients. For such analyses, data from both treated and untreated patient arms were utilized in order to discriminate treatment preditive genes from purely prognostic genes. For identifying treatment predictive genes for tamoxifen (TAM) response, both placebo and TAM-treated patients were included from NSABP Study B-14. In both studies, Cox proportional hazards models were utilized to examine the interaction between the treatment effect and gene expression. An interaction between treatment and gene expression exists if the treatment effect depends on the gene expression level; that is, if gene expression is a treatment predictive factor. Again, the likelihood ratio test was used to identify statistically significant predictive treatment genes by comparing the reduced model excluding the gene expression by treatment interaction versus the competing full model including the gene expression by treatment interaction.

Results

Table 2 reports the hazard ratio (H.R.) for recurrence versus variation in expression of genes and gene groups (axes), from analysis of the untreated NSABP B-14 trial patients (placebo arm).

The results shown in Table 2 are significant not only statistically but also in their H.R. magnitudes. It should be noted that for any marker a two fold change in H.R. from 1.0 changes the H.R. by 50%, and that each HR value describes the impact of a two fold change in expression of the marker variable relative to the average expression in the patient population. Thus, for example, Table 2 shows that for every two fold increase in expression of Proliferation Group or CCNB1 H.R. increases by approximately 50% (95% confidence limits span ~20% to ~90%).

TABLE 2

Univariate Analysis B14 Placebo Arm

| Variable | Estimate | P-value (LR) | H.R. | HRLowerCL | HRUpperCL |
|---|---|---|---|---|---|
| ProlGroup | 0.424845 | 0.0005 | 1.529353 | 1.204024 | 1.942588 |
| CCNB1_2 | 0.437596 | 0.0007 | 1.548979 | 1.204938 | 1.991252 |
| BIRC5_2 | 0.288646 | 0.0009 | 1.334619 | 1.12784 | 1.57931 |
| MYBL2_1 | 0.247787 | 0.0026 | 1.281188 | 1.090383 | 1.505381 |
| PGR_6 | −0.11734 | 0.0075 | 0.889281 | 0.8118 | 0.96829 |
| STK6_2 | 0.349493 | 0.0079 | 1.418348 | 1.098354 | 1.831569 |
| MKI67_2 | 0.238862 | 0.02 | 1.269803 | 1.03654 | 1.55556 |
| GSTM1_1 | −0.15 | 0.032 | 0.854961 | 0.742047 | 0.985056 |
| GAPD_1 | 0.305394 | 0.044 | 1.35716 | 1.00396 | 1.834618 |
| InvasionGroup | 0.253247 | 0.053 | 1.288201 | 0.994238 | 1.669079 |
| RPLP0_2 | −0.51811 | 0.056 | 0.595643 | 0.349143 | 1.016176 |
| ProlThres | 0.52227 | 0.061 | 1.685851 | 1.008598 | 2.817866 |
| MMP11_3 | 0.13374 | 0.083 | 1.143096 | 0.982561 | 1.329859 |

As shown in Table 2, thirteen variables (genes plus gene groups) correlated with recurrence H.R. with a p<0.1. As described above, because these correlations pertain to untreated patients, these variables are therefore statistically significant prognostic factors. The prognostic variables are: Proliferation Group; CCNB1; BIRC5; MYBL2; PGR; STK6; MKI67; GSTM1; GAPD; Invasion Group; RPLP0; Proliferation Threshold; MMP11. The Proliferation Group, Invasion Group, and Proliferation Threshold are defined components of the Recurrence Score algorithm.

Table 3 reports interaction analysis using results from both the placebo and TAM treatment arms of NSABP B14, carried out to identify variables that predict senstivity or resistance to TAM.

TABLE 3

B14 Placebo and TAM Combined Analysis of Interaction (Int)

| Variable | Estimate | P-value | H.R. | 95% CI for H.R. | |
|---|---|---|---|---|---|
| IntESR1_1 | −0.29602 | 0.000466 | 0.743775 | 0.630144 | 0.877896 |
| IntSCUBE2_2 | −0.21592 | 0.004183 | 0.805796 | 0.695108 | 0.934111 |
| IntESR1 Group | −0.27804 | 0.006669 | 0.757266 | 0.619458 | 0.925732 |
| IntTFRC_3 | 0.664542 | 0.027624 | 1.943601 | 1.075949 | 3.510933 |
| IntBCL2_2 | −0.26181 | 0.071688 | 0.769655 | 0.578846 | 1.023362 |

Increased expression of ten of these prognostic factors correlates with increased H.R.: Proliferation Group; CCNB1; BIRC5; MYBL2; STK6; MKI67; GAPD; Invasion Group; Proliferation threshold; MMP11. Seven of the ten markers for poor prognosis are are genes or gene sets that mark proliferating cells. Among these, the Proliferation Group (as defined in the Recurrence Score algorithm) is the top variable with respect to P-value. Increased expression three of the thirteen prognostic factors correlates with decreased H.R.: PGR, GSTM1, and RPLP0.

As shown, five variables (genes plus gene groups) correlate with response to TAM with p<0.1. These are ESR1, SCUBE2, ESR1 Group, TFRC, and BCL2. The most significant of these markers is ESR1. For every two fold increase in expression of ESR1, the H.R. for recurrence of TAM-treated patients decreases by about 25% (95% confidence limits span ~12% to ~37%). These data can be used as a continuous quantitative indication of a patient's likelihood of response to TAM. This is shown graphically in FIG. 1. It should be emphasized that all of the NSABP B-14 patients were classified as ER-positive, based on a clinically used assay and therefore candidates for TAM prescription. The present data demonstrate that within this "ER positive" population, patients experience variable levels of benefit on a predictable basis as a function of their ESR1 score.

This relationship between ESR1 expression and likelihood of therapeutic benefit from TAM can also be represented as a function of high, intermediate, and low ESR1 expression categories. ESR1 expression can be either represented in quartiles, tertiles or other divisions. For example, the data obtained in our study of the NSABP B14 patient population provide the following reference-normalized $C_T$ cutpoints for division of ESR1 expression by tertiles:

TABLE 4

ESR1 score cutpoints that categorize ESR1 expression by tertiles, using assay data from B-14 patients.

| ER neg | 0-33% ile | 33-67% ile | 67-100% ile |
|---|---|---|---|
| ESR1 < 6.5 | [6.5, 10.375) | [10.375, 11.41) | ER ≧ 11.41 |

Figure 2:
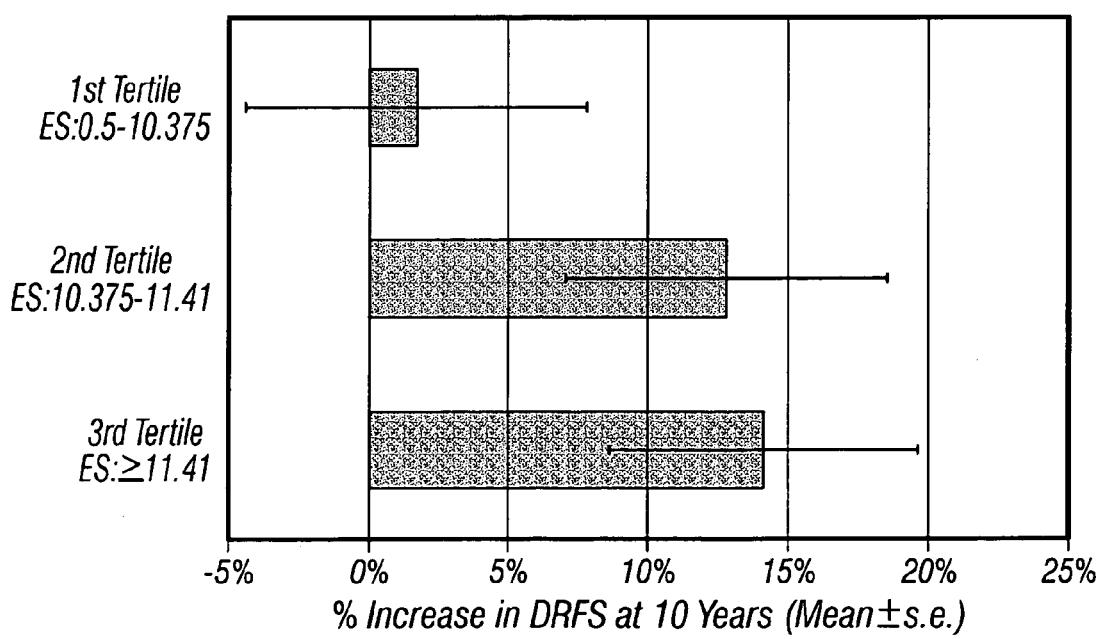
FIG. 2 shows the absolute benefit of tamoxifen (TAM) treatment as a function of ESR1 expression. The horizontal lines through bars represent 95% confidence limits.

FIG. 2, shows the absolute benefit of TAM amongst these three groups of patients as a function of ESR1 Expression (Horizontal lines through bars represent 95% confidence limits.)

As shown, TAM has substantial absolute benefit in the two-thirds of patients who express ESR1 at the highest levels, but has much less impact in patients in the lowest tertile of ESR1 expression.

Figure 3:
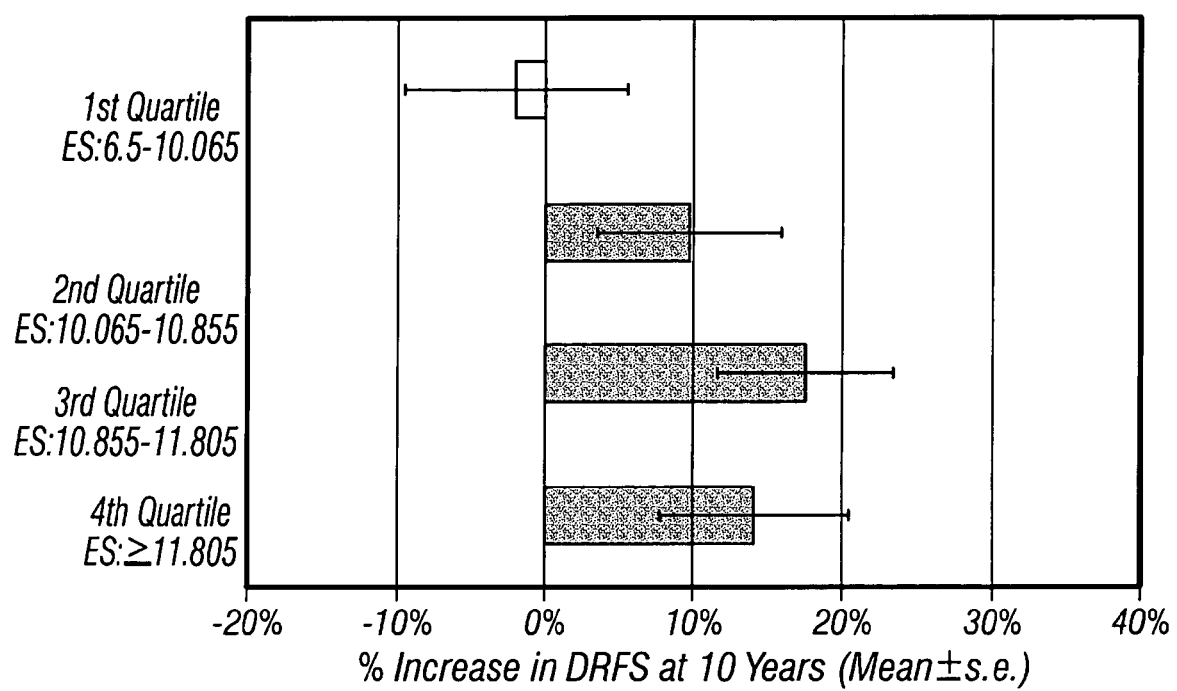
FIG. 3 shows the absolute benefit of TAM treatment as a function of the quartile into which the expression of ESR1 falls. The horizontal lines through bars represent 95% confidence limits. The cutpoints defining the quartiles of ESR1 expression, are based on reference-normalized $C_T$ values derived from analysis of the NSABP B-14 patient population.

Similarly the relationship between ESR1 expression and TAM benefit can be represented as a function of breaking ESR1 expression into quartiles. FIG. 3 shows the absolute benefit of TAM treatment as a function of quartiles of ESR1 expression (horizontal lines through bars represent 95% confidence limits). The cutpoints for ESR1 expression, are reference-normalized $C_T$s derived from analysis of the NSABP B14 patient population. As shown, patients in the lowest quartile of ESR1 expression experience little benefit from TAM.

ESR1 expression data can be used in conjunction with Recurrence Score to simultaneously determine whether a patient should be prescribed TAM or TAM plus chemotherapy. Table 6, which presents data from analysis of both arms of NSABP B14, illustrates this, as well as the format for conveying these data. To illustrate how this Table might be used, patients in the low recurrence risk category as defined by RS, who express ESR1 in the upper 75th percentile are logical candidates to be treated with TAM alone. Patients who have low recurrence risk, but are in the lower 25th percentile in ESR1 expression and for whom risk of TAM side effects is a particular concern may reasonably be considered patients for whom TAM treatment is less appropriate. Patients at high risk who express ER above the 25th percentile are logical candidates for treatment with both TAM and chemotherapy.

TABLE 5

NSABP Patient Distributions by RS and ESR1 Expression Categories

| RS Group | ER 75th-100th % ile | ER 50th-75th % ile | ER 25th-50th % ile | ER 0-25th % ile | ER neg | Row Totals |
|---|---|---|---|---|---|---|
| Low risk | 101 | 89 | 82 | 41 | 0 | 313 |
| Int risk | 29 | 45 | 37 | 42 | 1 | 154 |
| High Risk | 24 | 23 | 32 | 71 | 28 | 178 |
| All Grps | 154 | 157 | 151 | 154 | 29 | 645 |

(The number within each cell is the number of assayed B-14 patients in the indicated category).

Based on the following reference-normalized ESR1 cutoff points:

TABLE 6

| ER neg | 0-25% ile | 25-50% ile | 50-75% ile | 75-100% ile |
|---|---|---|---|---|
| ER < 6.5 | [6.5, 10.065) | [10.065, 10.855) | [10.855, 11.805) | ER >= 11.805 |

The following illustrations indicate how Table 5 can be used to make decisions about treatment of a patient with anti-estrogen and/or chemotherapy.

Recommend Hormonal Therapy

| RS Group | ER 75th-100th % ile | ER 50th-75th % ile | ER 25th-50th % ile | ER 0-25th % ile | ER neg | Row Totals |
|---|---|---|---|---|---|---|
| Low risk | 101 | 89 | 82 | 41 | 0 | 313 |
| Int risk | ~~29~~ | ~~45~~ | ~~37~~ | 42 | 1 | 154 |
| High Risk | 24 | 23 | 32 | 71 | 28 | 178 |
| All Grps | 154 | 157 | 151 | 154 | 29 | 645 |

Recommend Hormonal Therapy, Consider Chemotherapy

| RS Group | ER 75th-100th % ile | ER 50th-75th % ile | ER 25th-50th % ile | ER 0-25th % ile | ER neg | Row Totals |
|---|---|---|---|---|---|---|
| Low risk | 101 | 89 | 82 | 41 | 0 | 313 |
| Int risk | 29 | 45 | 37 | 42 | 1 | 154 |
| High Risk | 24 | 23 | 32 | 71 | 28 | 178 |
| All Grps | 154 | 157 | 151 | 154 | 29 | 645 |

Recommend Hormonal Therapy + Chemotherapy

| RS Group | ER 75th-100th % ile | ER 50th-75th % ile | ER 25th-50th % ile | ER 0-25th % ile | ER neg | Row Totals |
|---|---|---|---|---|---|---|
| Low risk | 101 | 89 | 82 | 41 | 0 | 313 |
| Int risk | 29 | ~~45~~ | ~~37~~ | ~~42~~ | 1 | 154 |
| High Risk | 24 | 23 | 32 | 71 | 28 | 178 |
| All Grps | 154 | ~~157~~ | ~~151~~ | ~~154~~ | 29 | 645 |

All references cited throughout the disclosure are hereby expressly incorporated by reference.

One skilled in the art will recognize numerous methods and materials similar or equivalent to those described herein, which could be used in the practice of the present invention. Indeed, the present invention is in no way limited to the methods and materials described. While the present invention has been described with reference to what are considered to be the specific embodiments, it is to be understood that the invention is not limited to such embodiments. To the contrary; the invention is intended to cover various modifications and equivalents included within the spirit and scope of the appended claims. For example, while the disclosure is illustrated by identifying genes and groups of genes useful in predicting the beneficial response of a breast cancer patient to treatment with TAM, similar methods to determine patient response to treatment with other anti-estrogen drugs, as well as similar genes, gene sets and methods concerning other types of cancer are specifically within the scope herein.

TABLE 7

| Reagent | Gene | Accession | Oligo | Sequence | Length | |
|---|---|---|---|---|---|---|
| Forward | ACTB | NM_001101 | S0034/B-acti.f2 | CAGCAGATGTGGATCAGCAAG | 21 | SEQ ID NO: 1 |
| Reverse | ACTB | NM_001101 | S0036/B-acti.r2 | GCATTTGCGGTGGACGAT | 18 | SEQ ID NO: 2 |
| Probe | ACTB | NM_001101 | S4730/B-acti.p2 | AGGAGTATGACGAGTCCGGCCCC | 23 | SEQ ID NO: 3 |
| Forward | BAG1 | NM_004323 | S1386/BAG1.f2 | CGTTGTCAGCACTTGGAATACAA | 23 | SEQ ID NO: 4 |
| Reverse | BAG1 | NM_004323 | S1387/BAG1.r2 | GTTCAACCTCTTCCTGTGGACTGT | 24 | SEQ ID NO: 5 |
| Probe | BAG1 | NM_004323 | S4731/BAG1.p2 | CCCAATTAACATGACCCGGCAACCAT | 26 | SEQ ID NO: 6 |
| Forward | BCL2 | NM_000633 | S0043/Bcl2.f2 | CAGATGGACCTAGTACCCACTGAGA | 25 | SEQ ID NO: 7 |
| Reverse | BCL2 | NM_000633 | S0045/Bcl2.r2 | CCTATGATTTAAGGGCATTTTTCC | 24 | SEQ ID NO: 8 |
| Probe | BCL2 | NM_000633 | S4732/Bcl2.p2 | TTCCACGCCGAAGGACAGCGAT | 22 | SEQ ID NO: 9 |
| Forward | CCNB1 | NM_031966 | S1720/CCNB1.f2 | TTCAGGTTGTTGCAGGAGAC | 20 | SEQ ID NO: 10 |
| Reverse | CCNB1 | NM_031966 | S1721/CCNB1.r2 | CATCTTCTTGGGCACACAAT | 20 | SEQ ID NO: 11 |
| Probe | CCNB1 | NM_031966 | S4733/CCNB1.p2 | TGTCTCCATTATTGATCGGTTCATGCA | 27 | SEQ ID NO: 12 |
| Forward | CD68 | NM_001251 | S0067/CD68.f2 | TGGTTCCCAGCCCTGTGT | 18 | SEQ ID NO: 13 |
| Reverse | CD68 | NM_001251 | S0069/CD68.r2 | CTCCTCCACCCTGGGTTGT | 19 | SEQ ID NO: 14 |
| Probe | CD68 | NM_001251 | S4734/CD68.p2 | CTCCAAGCCCAGATTCAGATTCGAGTCA | 28 | SEQ ID NO: 15 |
| Forward | SCUBE2 | NM_020974 | S1494/SCUBE2.f2 | TGACAATCAGCACACCTGCAT | 21 | SEQ ID NO: 16 |
| Reverse | SCUBE2 | NM_020974 | S1495/SCUBE2.r2 | TGTGACTACAGCCGTGATCCTTA | 23 | SEQ ID NO: 17 |
| Probe | SCUBE2 | NM_020974 | S4735/SCUBE2.p2 | CAGGCCCTCTTCCGAGCGGT | 20 | SEQ ID NO: 18 |
| Forward | CTSL2 | NM_001333 | S4354/CTSL2.f1 | TGTCTCACTGAGCGAGCAGAA | 21 | SEQ ID NO: 19 |
| Reverse | CTSL2 | NM_001333 | S4355/CTSL2.r1 | ACCATTGCAGCCCTGATTG | 19 | SEQ ID NO: 20 |
| Probe | CTSL2 | NM_001333 | S4356/CTSL2.p1 | CTTGAGGACGCGAACAGTCCACCA | 24 | SEQ ID NO: 21 |
| Forward | ESR1 | NM_000125 | S0115/EstR1.f1 | CGTGGTGCCCCTCTATGAC | 19 | SEQ ID NO: 22 |
| Reverse | ESR1 | NM_000125 | S0117/EstR1.r1 | GGCTAGTGGGCGCATGTAG | 19 | SEQ ID NO: 23 |
| Probe | ESR1 | NM_000125 | S4737/EstR1.p1 | CTGGAGATGCTGGACGCCC | 19 | SEQ ID NO: 24 |
| Forward | GAPD | NM_002046 | S0374/GAPD.f1 | ATTCCACCCATGGCAAATTC | 20 | SEQ ID NO: 25 |
| Reverse | GAPD | NM_002046 | S0375/GAPD.r1 | GATGGGATTTCCATTGATGACA | 22 | SEQ ID NO: 26 |
| Probe | GAPD | NM_002046 | S4738/GAPD.p1 | CCGTTCTCAGCCTTGACGGTGC | 22 | SEQ ID NO: 27 |
| Forward | GRB7 | NM_005310 | S0130/GRB7.f2 | CCATCTGCATCCATCTTGTT | 20 | SEQ ID NO: 28 |
| Reverse | GRB7 | NM_005310 | S0132/GRB7.r2 | GGCCACCAGGGTATTATCTG | 20 | SEQ ID NO: 29 |
| Probe | GRB7 | NM_005310 | S4726/GRB7.p2 | CTCCCCACCCTTGAGAAGTGCCT | 23 | SEQ ID NO: 30 |
| Forward | GSTM1 | NM_000561 | S2026/GSTM1.r1 | GGCCCAGCTTGAATTTTTCA | 20 | SEQ ID NO: 31 |
| Reverse | GSTM1 | NM_000561 | S2027/GSTM1.f1 | AAGCTATGAGGAAAAGAAGTACACGAT | 27 | SEQ ID NO: 32 |
| Probe | GSTM1 | NM_000561 | S4739/GSTM1.p1 | TCAGCCACTGGCTTCTGTCATAATCAGGAG | 30 | SEQ ID NO: 33 |
| Forward | GUSB | NM_000181 | S0139/GUS.f1 | CCCACTCAGTAGCCAAGTCA | 20 | SEQ ID NO: 34 |
| Reverse | GUSB | NM_000181 | S0141/GUS.r1 | CACGCAGGTGGTATCAGTCT | 20 | SEQ ID NO: 35 |
| Probe | GUSB | NM_000181 | S4740/GUS.p1 | TCAAGTAAACGGGCTGTTTTCCAAACA | 27 | SEQ ID NO: 36 |
| Forward | ERBB2 | NM_004448 | S0142/HER2.f3 | CGGTGTGAGAAGTGCAGCAA | 20 | SEQ ID NO: 37 |
| Reverse | ERBB2 | NM_004448 | S0144/HER2.r3 | CCTCTCGCAAGTGCTCCAT | 19 | SEQ ID NO: 38 |
| Probe | ERBB2 | NM_004448 | S4729/HER2.p3 | CCAGACCATAGCACACTCGGGCAC | 24 | SEQ ID NO: 39 |

TABLE 7-continued

| Reagent | Gene | Accession | Oligo | Sequence | Length | |
|---|---|---|---|---|---|---|
| Forward | MKI67 | NM_002417 | S0436/MKI67.f2 | CGGACTTTGGGTGCGACTT | 19 | SEQ ID NO: 40 |
| Reverse | MKI67 | NM_002417 | S0437/MKI67.r2 | TTACAACTCTTCCACTGGGACGAT | 24 | SEQ ID NO: 41 |
| Probe | MKI67 | NM_002417 | S4741/MKI67.p2 | CCACTTGTCGAACCACCGCTCGT | 23 | SEQ ID NO: 42 |
| Forward | MYBL2 | NM_002466 | S3270/MYBL2.f1 | GCCGAGATCGCCAAGATG | 18 | SEQ ID NO: 43 |
| Reverse | MYBL2 | NM_002466 | S3271/MYBL2.r1 | CTTTTGATGGTAGAGTTCCAGTGATTC | 27 | SEQ ID NO: 44 |
| Probe | MYBL2 | NM_002466 | S4742/MYBL2.p1 | CAGCATTGTCTGTCCTCCCTGGCA | 24 | SEQ ID NO: 45 |
| Forward | PGR | NM_000926 | S1336/PR.f6 | GCATCAGGCTGTCATTATGG | 20 | SEQ ID NO: 46 |
| Reverse | PGR | NM_000926 | S1337/PR.r6 | AGTAGTTGTGCTGCCCTTCC | 20 | SEQ ID NO: 47 |
| Probe | PGR | NM_000926 | S4743/PR.p6 | TGTCCTTACCTGTGGGAGCTGTAAGGTC | 28 | SEQ ID NO: 48 |
| Forward | RPLP0 | NM_001002 | S0256/RPLPO.f2 | CCATTCTATCATCAACGGGTACAA | 24 | SEQ ID NO: 49 |
| Reverse | RPLP0 | NM_001002 | S0258/RPLPO.r2 | TCAGCAAGTGGGAAGGTGTAATC | 23 | SEQ ID NO: 50 |
| Probe | RPLP0 | NM_001002 | S4744/RPLPO.p2 | TCTCCACAGACAAGGCCAGGACTCG | 25 | SEQ ID NO: 51 |
| Forward | STK6 | NM_003600 | S0794/STK6.f2 | CATCTTCCAGGAGGACCACT | 20 | SEQ ID NO: 52 |
| Reverse | STK6 | NM_003600 | S0795/STK6.r2 | TCCGACCTTCAATCATTTCA | 20 | SEQ ID NO: 53 |
| Probe | STK6 | NM_003600 | S4745/STK6.p2 | CTCTGTGGCACCCTGGACTACTG | 24 | SEQ ID NO: 54 |
| Forward | MMP11 | NM_005940 | S2067/MMP11.f3 | CCTGGAGGCTGCAACATACC | 20 | SEQ ID NO: 55 |
| Reverse | MMP11 | NM_005940 | S2068/MMP11.r3 | TACAATGGCTTTGGAGGATAGCA | 23 | SEQ ID NO: 56 |
| Probe | MMP11 | NM_005940 | S4746/MMP11.p3 | ATCCTCCTGAAGCCCTTTTCGCAGC | 25 | SEQ ID NO: 57 |
| Forward | BIRC5 | NM_001168 | S0259/BIRC5.f2 | TGTTTTGATTCCCGGGCTTA | 20 | SEQ ID NO: 58 |
| Reverse | BIRC5 | NM_001168 | S0261/BIRC5.r2 | CAAAGCTGTCAGCTCTAGCAAAAG | 24 | SEQ ID NO: 59 |
| Probe | BIRC5 | NM_001168 | S4747/BIRC5.p2 | TGCCTTCTTCCTCCCTCACTTCTCACCT | 28 | SEQ ID NO: 60 |
| Forward | TFRC | NM_003234 | S1352/TFRC.f3 | GCCAACTGCTTTCATTTGTG | 20 | SEQ ID NO: 61 |
| Reverse | TFRC | NM_003234 | S1353/TFRC.r3 | ACTCAGGCCCATTTCCTTTA | 20 | SEQ ID NO: 62 |
| Probe | TFRC | NM_003234 | S4748/TFRC.p3 | AGGGATCTGAACCAATACAGAGCAGACA | 28 | SEQ ID NO: 63 |

TABLE 8

| Gene | LocusLink | Sequence |
|---|---|---|
| ACTB | NM_001101 | CAGCAGATGTGGATCAGCAAGCAGGAGTATGACGAGTCCGGCCCCTCCATCGTCCACCGCAAATGC<br>SEQ ID NO: 64 |
| BAG1 | NM_004323 | CGTTGTCAGCACTTGGAATACAAGATGGTTGCCGGGTCATGTTAATTGGGAAAAAGAACAGTCCACAGGAAGAGGTTGAAC<br>SEQ ID NO: 65 |
| BCL2 | NM_000633 | CAGATGGACCTAGTACCCACTGAGATTTCCACGCCGAAGGACAGCGATGGGAAAATGCCCTTAAATCATAGG<br>SEQ ID NO: 66 |
| CCNB1 | NM_031966 | TTCAGGTTGTTGCAGGAGACCATGTACATGACTGTCTCCATTATTGATCGGTTCATGCAGAATAATTGTGTGCCCAAGAAGATG<br>SEQ ID NO: 67 |
| CD68 | NM_001251 | TGTTCCCAGCCCTGTGTCCACCTCCAAGCCCAGATTCAGATTCGAGTCATGTACACAACCCAGGGTGGAGGAG<br>SEQ ID NO: 68 |
| SCUBE2 | NM_020974 | TGACAATCAGCACACCTGCATTCACCGCTCGGAAGAGGGCCTGAGCTGCATGAATAAGGATCACGGCTGTAGTCACA<br>SEQ ID NO: 69 |

TABLE 8-continued

| Gene | LocusLink | Sequence |
|---|---|---|
| CTSL2 | NM_001333 | TGTCTCACTGAGCGAGCAGAATCTGGTGGACTGTTCGCGTCCTCAAGGCAATCAGGGCTGCAATGGT<br>SEQ ID NO: 70 |
| ESR1 | NM_000125 | CGTGGTGCCCCTCTATGACCTGCTGCTGGAGATGCTGGACGCCCACCGCCTACATGCGCCCACTAGCC<br>SEQ ID NO: 71 |
| GAPD | NM_002046 | ATTCCACCCATGGCAAATTCCATGGCACCGTCAAGGCTGAGAACGGGAAGCTTGTCATCAATGGAAATCCCATC<br>SEQ ID NO: 72 |
| GRB7 | NM_005310 | CCATCTGCATCCATCTTGTTTGGGCTCCCCACCCTTGAGAAGTGCCTCAGATAATACCCTGGTGGCC<br>SEQ ID NO: 73 |
| GSTM1 | NM_000561 | AAGCTATGAGGAAAGAAGTACACGATGGGGGACGCTCCTGATTATGACAGAAGCCAGTGGCTGAATGAAAAATTCAAGCTGGGCC<br>SEQ ID NO: 74 |
| GUSB | NM_000181 | CCCACTCAGTAGCCAAGTCACAATGTTTGGAAAACAGCCCGTTTACTTGAGCAAGACTGATACCACCTGCGTG<br>SEQ ID NO: 75 |
| ERBB2 | NM_004448 | CGGTGTGAGAAGTGCAGCAAGCCCTGTGCCCGAGTGTGCTATGGTCTGGGCATGGAGCACTTGCGAGAGG<br>SEQ ID NO: 76 |
| MKI67 | NM_002417 | CGGACTTTGGGTGCGACTTGACGAGCGGTGGTTCGACAAGTGGCCTTGCGGGCCGGATCGTCCCAGTGGAAGAGTTGTAA<br>SEQ ID NO: 77 |
| MYBL2 | NM_002466 | GCCGAGATCGCCAAGATGTTGCCAGGGAGGACAGACAATGCTGTGAAGAATCACTGGAACTCTACCATCAAAAG<br>SEQ ID NO: 78 |
| PGR | NM_000926 | GCATCAGGCTGTCATTATGGTGTCCTTACCTGTGGGAGCTGTAAGGTCTTCTTTAAGAGGGCAATGGAAGGGCAGCACAACTACT<br>SEQ ID NO: 79 |
| RPLP0 | NM_001002 | CCATTCTATCATCAACGGGTACAAACGAGTCCTGGCCTTGTCTGTGGAGACGGATTACACCTTCCCACTGCTGA<br>SEQ ID NO: 80 |
| STK6 | NM_003600 | CATCTTCCAGGAGGACCACTCTCTGTGGCACCCTGGACTACCTGCCCCCTGAAATGATTGAAGGTCGGA<br>SEQ ID NO: 81 |
| MMP11 | NM_005940 | CCTGGAGGCTGCAACATACCTCAATCCTGTCCCAGGCCGGATCCTCCTGAAGCCCTTTTCGCAGCACTGCTATCCTCCAAAGCCATTGTA<br>SEQ ID NO: 82 |
| BIRC5 | NM_001168 | TGTTTTGATTCCCGGGCTTACCAGGTGAGAAGTGAGGGAGGAAGAAGGCAGTGTCCCTTTTGCTAGAGCTGACAGCTTTG<br>SEQ ID NO: 83 |
| TFRC | NM_003234 | GCCAACTGCTTTCATTTGTGAGGGATCTGAACCAATACAGAGCAGACATAAAGGAAATGGGCCTGAGT<br>SEQ ID NO: 84 |

What is claimed:

1. A method comprising: measuring, in a tumor sample obtained from a patient with estrogen receptor (ESR1) positive (>10 fmol/mg cytosol protein) breast cancer, an ESR1 Group Score or ESR1, BCL2 and SCUBE2 RNA transcript expression levels; calculating a predictive score based on the ESR1 Group Score or expression levels of said RNA transcripts to determine the likelihood that said patient has an increased likelihood of a beneficial response to treatment with an anti-estrogen drug, wherein increases in the ESR1 Group Score, or in the expression levels of said RNA transcripts positively correlate with an increased likelihood of a beneficial response to said treatment, and generating a report based on the predictive score.

2. The method of claim 1 wherein the expression level of the ESR1 Group Score or said RNA transcripts is determined by reverse transcriptase polymerase chain reaction (RT-PCR).

3. The method of claim 1 wherein the anti-estrogen drug is selected from the group consisting of tamoxifen, toremifene, anastrozole, and megasterol acetate.

4. The method of claim 3 wherein the anti-estrogen drug is tamoxifen.

5. The method of claim 1 wherein the report
further comprises information whether said patient should receive treatment with said anti-estrogen drug alone, chemotherapy alone, or chemotherapy plus anti-estrogen drug.

6. The method of claim 5 wherein said treatment with
anti-estrogen alone, chemotherapy alone, or chemotherapy plus anti-estrogen is recommended by consulting a graph or a table along one axis of which ESR1 expression level is displayed, either as a continuous variable or in ESR1 expression ranges, and along the other axis of which likelihood of cancer recurrence is displayed, either as a continuous variable or in risk ranges.

7. The method of claim 1 further comprising the step of determining a Recurrence Score and an ESR1 score based on the expression level of the RNA transcript of ESR1 for said patient.

8. The method of claim 7 wherein the report further comprises ESR1 expression and Recurrence Score ranges for a population of breast cancer patients, arranged in tertiles.

9. The method of claim 8 wherein said ranges are low, intermediate and high ESR1 expression and recurrence risk ranges.

10. The method of claim 7 wherein if said patient has an ESR1 score in the high ESR1 range and a Recurrence Score in the low recurrence risk range, this would suggest treatment with an anti-estrogen drug alone.

11. The method of claim 7 wherein
if said patient has an ESR1 score in the low ESR1 range and a Recurrence Score in the high recurrence risk range, this would suggest treatment with chemotherapy alone.

12. The method of claim 7 wherein
if said patient has an ESR1 score in the intermediate ESR1 range and a Recurrence Score in the high recurrence risk range, this would suggest treatment with both an anti-estrogen drug and chemotherapy.

* * * * *